(12) United States Patent
Kugler et al.

(10) Patent No.: US 10,874,400 B2
(45) Date of Patent: Dec. 29, 2020

(54) METHODS AND APPARATUS FOR TREATING BODY TISSUE SPHINCTERS AND THE LIKE

(71) Applicant: Torax Medical, Inc., Shoreview, MN (US)

(72) Inventors: Chad J. Kugler, Buffalo, MN (US); Jerome K. Grudem, Jr., Rogers, MN (US); Todd A. Berg, Stillwater, MN (US); William J. Swanson, St. Paul, MN (US)

(73) Assignee: Torax Medical, Inc., Shoreview, MN (US)

( * ) Notice: Subject to any disclaimer, the term of this patent is extended or adjusted under 35 U.S.C. 154(b) by 195 days.

(21) Appl. No.: 16/204,043

(22) Filed: Nov. 29, 2018

(65) Prior Publication Data

US 2019/0167269 A1 Jun. 6, 2019

Related U.S. Application Data

(60) Continuation of application No. 14/445,723, filed on Jul. 29, 2014, now Pat. No. 10,398,440, which is a
(Continued)

(51) Int. Cl.
*A61B 17/12* (2006.01)
*A61F 2/00* (2006.01)
(Continued)

(52) U.S. Cl.
CPC .. *A61B 17/12009* (2013.01); *A61B 17/12013* (2013.01); *A61F 2/0036* (2013.01);
(Continued)

(58) Field of Classification Search
CPC .... A61B 17/12009; A61B 2017/00876; A61B 2017/00827; A61F 5/005
See application file for complete search history.

(56) References Cited

U.S. PATENT DOCUMENTS

| 281,371 A | 7/1883 | Keller |
| 3,495,620 A | 2/1970 | Bazell et al. |

(Continued)

FOREIGN PATENT DOCUMENTS

| CA | 2480343 | 10/2003 | |
| DE | 3011742 | * 10/1981 | ............... A61F 5/44 |

(Continued)

OTHER PUBLICATIONS

"GI Endoscopy: Therapies for GERD," Medtech Insight, Sep. 2001, p. 236.
(Continued)

*Primary Examiner* — Sarah A Simpson
(74) *Attorney, Agent, or Firm* — Frost Brown Todd LLC

(57) ABSTRACT

A plurality of structures that resiliently attract one another are provided for implanting in a patient around a body tissue structure of the patient. For example, the body tissue structure may be the esophagus, and the plurality of structures may be implanted in an annulus around the outside of the esophagus, the annulus being substantially coaxial with the esophagus. The attraction may be between annularly adjacent ones of the structures in the annulus, and it may be provided, for example, by magnets or springs. The array of structures is preferably self-limiting with respect to the smallest area that it can encompass, and this smallest area is preferably large enough to prevent the apparatus from applying excessive pressure to tissue passing through that area.

20 Claims, 21 Drawing Sheets

Related U.S. Application Data division of application No. 13/403,441, filed on Feb. 23, 2012, now abandoned, which is a division of application No. 12/610,633, filed on Nov. 2, 2009, now Pat. No. 8,187,164, which is a continuation of application No. 11/147,801, filed on Jun. 7, 2005, now Pat. No. 7,695,427.

(60) Provisional application No. 60/653,966, filed on Feb. 17, 2005, provisional application No. 60/614,835, filed on Sep. 30, 2004, provisional application No. 60/599,333, filed on Aug. 5, 2004.

(51) Int. Cl.
*A61F 5/00* (2006.01)
*A61B 17/00* (2006.01)

(52) U.S. Cl.
CPC ............ *A61F 5/005* (2013.01); *A61F 5/0069* (2013.01); *A61B 2017/00827* (2013.01); *A61B 2017/00876* (2013.01); *A61B 2017/12018* (2013.01)

(56) References Cited

U.S. PATENT DOCUMENTS

| | | |
|---|---|---|
| 3,642,004 A | 2/1972 | Osthagen et al. |
| 3,750,194 A | 8/1973 | Summers |
| 3,798,729 A | 3/1974 | Tanaka et al. |
| 3,810,259 A | 5/1974 | Summers et al. |
| 3,812,841 A | 5/1974 | Isaacson et al. |
| 3,863,622 A | 2/1975 | Buuck et al. |
| 3,875,928 A | 4/1975 | Angelchik |
| 3,926,175 A | 12/1975 | Allen et al. |
| 3,939,821 A | 2/1976 | Roth |
| 3,952,726 A | 4/1976 | Hennig et al. |
| 3,991,743 A | 11/1976 | Bucalo et al. |
| 4,024,855 A | 5/1977 | Bucalo et al. |
| 4,053,952 A | 10/1977 | Goldstein et al. |
| 4,154,226 A | 5/1979 | Hennig et al. |
| 4,197,840 A | 4/1980 | Beck et al. |
| 4,209,010 A | 6/1980 | Ward et al. |
| 4,258,705 A | 3/1981 | Sorenson et al. |
| 4,271,827 A | 6/1981 | Angelchik et al. |
| D271,478 S | 11/1983 | Kelman |
| 4,412,530 A | 11/1983 | Burton et al. |
| 4,595,390 A | 6/1986 | Hakim et al. |
| 4,652,257 A | 3/1987 | Chang et al. |
| 4,773,393 A | 9/1988 | Haber et al. |
| 4,786,276 A | 11/1988 | Haber et al. |
| 4,832,680 A | 5/1989 | Haber et al. |
| 4,865,588 A | 9/1989 | Flinchbaugh et al. |
| 4,969,474 A | 11/1990 | Schwarz et al. |
| 4,994,019 A | 2/1991 | Fernandez et al. |
| 5,004,454 A | 4/1991 | Beyar et al. |
| 5,007,940 A | 4/1991 | Berg et al. |
| 5,041,092 A | 8/1991 | Barwick et al. |
| 5,088,979 A | 2/1992 | Filipi et al. |
| 5,140,999 A | 8/1992 | Ardito et al. |
| 5,160,338 A | 11/1992 | Vincent et al. |
| 5,176,618 A | 1/1993 | Freedman et al. |
| 5,234,447 A | 8/1993 | Kaster et al. |
| 5,234,448 A | 8/1993 | Wholey et al. |
| 5,236,410 A | 8/1993 | Granov et al. |
| 5,254,126 A | 10/1993 | Filipi et al. |
| 5,336,263 A | 8/1994 | Ersek et al. |
| 5,366,506 A | 11/1994 | Davis et al. |
| 5,387,235 A | 2/1995 | Chuter et al. |
| 5,397,355 A | 3/1995 | Marin et al. |
| 5,403,326 A | 4/1995 | Harrison et al. |
| 5,411,552 A | 5/1995 | Andersen et al. |
| 5,451,406 A | 9/1995 | Lawin et al. |
| 5,509,888 A | 4/1996 | Miller et al. |
| 5,562,598 A | 10/1996 | Whalen et al. |
| 5,593,443 A | 1/1997 | Carter et al. |
| 5,655,546 A | 8/1997 | Halpern et al. |
| 5,695,504 A | 12/1997 | Gifford, III et al. |
| 5,713,877 A | 2/1998 | Davis et al. |
| 5,725,554 A | 3/1998 | Simon et al. |
| 5,755,658 A | 5/1998 | Wallace et al. |
| 5,762,599 A | 6/1998 | Sohn et al. |
| 5,827,321 A | 10/1998 | Roubin et al. |
| 5,843,164 A | 12/1998 | Frantzen et al. |
| 5,861,036 A | 1/1999 | Godin et al. |
| 5,876,448 A | 3/1999 | Thompson et al. |
| 5,887,594 A | 3/1999 | LoCicero |
| 5,896,756 A | 4/1999 | Watkins et al. |
| 5,919,233 A | 7/1999 | Knopf et al. |
| 5,954,506 A | 9/1999 | Tanaka |
| 5,957,949 A | 9/1999 | Leonhardt et al. |
| 5,997,467 A | 12/1999 | Connolly et al. |
| 6,015,431 A | 1/2000 | Thornton et al. |
| 6,019,789 A | 2/2000 | Dinh et al. |
| 6,050,982 A | 4/2000 | Wheeler et al. |
| 6,056,744 A | 5/2000 | Edwards et al. |
| 6,073,052 A | 6/2000 | Zelickson et al. |
| 6,074,341 A | 6/2000 | Anderson et al. |
| 6,106,548 A | 8/2000 | Roubin et al. |
| 6,136,006 A | 10/2000 | Johnson et al. |
| 6,146,416 A | 11/2000 | Andersen et al. |
| 6,168,621 B1 | 1/2001 | Vrba et al. |
| 6,171,231 B1 | 1/2001 | Connolly et al. |
| 6,173,715 B1 | 1/2001 | Sinanan et al. |
| 6,190,406 B1 | 2/2001 | Duerig et al. |
| 6,203,569 B1 | 3/2001 | Wijay et al. |
| 6,231,561 B1 | 5/2001 | Frazier et al. |
| 6,251,064 B1 | 6/2001 | Silverman et al. |
| 6,254,642 B1 | 7/2001 | Taylor et al. |
| 6,264,687 B1 | 7/2001 | Tomonto et al. |
| 6,296,607 B1 | 10/2001 | Milbocker et al. |
| 6,302,917 B1 | 10/2001 | Dua et al. |
| 6,348,033 B1 * | 2/2002 | Catlett ..................... A61N 2/00 600/15 |
| 6,409,656 B1 | 6/2002 | Sangouard et al. |
| 6,409,723 B1 | 6/2002 | Edwards |
| 6,419,701 B1 | 7/2002 | Cook et al. |
| 6,432,038 B1 | 8/2002 | Bakane et al. |
| 6,432,040 B1 | 8/2002 | Meah |
| 6,447,533 B1 | 9/2002 | Adams |
| 6,451,048 B1 | 9/2002 | Berg et al. |
| 6,460,262 B1 | 10/2002 | Cabak et al. |
| 6,464,628 B1 | 10/2002 | Forsell et al. |
| 6,475,236 B1 | 11/2002 | Roubin et al. |
| 6,497,647 B1 | 12/2002 | Tucker |
| 6,511,491 B2 | 1/2003 | Grudem et al. |
| 6,530,934 B1 | 3/2003 | Jacobsen et al. |
| 6,544,291 B2 | 4/2003 | Taylor et al. |
| 6,547,776 B1 | 4/2003 | Gaiser et al. |
| 6,551,328 B2 | 4/2003 | Korlenbach |
| 6,558,429 B2 | 5/2003 | Taylor et al. |
| 6,572,605 B1 | 6/2003 | Humes et al. |
| 6,592,596 B1 | 7/2003 | Geitz |
| 6,595,909 B2 | 7/2003 | Silverman et al. |
| 6,596,004 B1 | 7/2003 | Regnault et al. |
| 6,604,529 B2 | 8/2003 | Kim |
| 6,609,522 B2 | 8/2003 | Cheng et al. |
| 6,663,639 B1 | 12/2003 | Laufer et al. |
| 6,695,878 B2 | 2/2004 | McGuckin et al. |
| 6,730,014 B2 | 5/2004 | Wilk et al. |
| 6,736,828 B1 | 5/2004 | Adams et al. |
| 6,764,518 B2 | 7/2004 | Godin et al. |
| 6,776,789 B2 | 8/2004 | Bryant et al. |
| 6,830,588 B2 | 12/2004 | Furukawa et al. |
| 6,835,200 B2 | 12/2004 | Laufer et al. |
| D506,943 S | 7/2005 | Erickson |
| 6,960,221 B2 | 11/2005 | Ho et al. |
| 6,960,233 B1 | 11/2005 | Berg et al. |
| 7,025,791 B2 | 4/2006 | Levine et al. |
| 7,060,080 B2 | 6/2006 | Bachmann et al. |
| 7,087,088 B2 | 8/2006 | Berg et al. |
| 7,115,879 B2 | 10/2006 | Leach et al. |
| 7,238,191 B2 | 7/2007 | Bachmann |
| 7,288,101 B2 | 10/2007 | Deem et al. |

(56) References Cited

U.S. PATENT DOCUMENTS

| | | |
|---|---|---|
| 7,328,707 B2 | 2/2008 | Durgin et al. |
| 7,331,969 B1 | 2/2008 | Inganas et al. |
| 7,400,926 B2 | 7/2008 | Forsell et al. |
| 7,445,010 B2 | 11/2008 | Kugler et al. |
| 7,458,930 B2 | 12/2008 | Meretei et al. |
| 7,468,060 B2 | 12/2008 | Utley et al. |
| 7,488,336 B2 | 2/2009 | Benchetrit et al. |
| 7,497,822 B1 | 3/2009 | Kugler et al. |
| 7,566,297 B2 | 7/2009 | Banik et al. |
| 7,662,087 B2 | 2/2010 | Bailly et al. |
| 7,695,427 B2 | 4/2010 | Kugler et al. |
| 7,775,966 B2 | 8/2010 | Dlugos et al. |
| 7,775,967 B2 | 8/2010 | Gertner et al. |
| 7,811,298 B2 | 10/2010 | Birk et al. |
| 7,811,299 B2 | 10/2010 | Bachmann et al. |
| 7,879,068 B2 | 2/2011 | Dlugos et al. |
| 7,901,418 B2 | 3/2011 | Danitz et al. |
| 8,187,164 B2 | 5/2012 | Kugler et al. |
| 10,398,440 B2 | 9/2019 | Kugler et al. |
| 2001/0020189 A1 | 9/2001 | Taylor |
| 2002/0078967 A1 | 6/2002 | Sixto et al. |
| 2002/0082621 A1 | 6/2002 | Schurr et al. |
| 2002/0198548 A1 | 12/2002 | Robert |
| 2003/0018377 A1 | 1/2003 | Berg et al. |
| 2003/0153806 A1 | 8/2003 | Miller |
| 2003/0199987 A1 | 10/2003 | Berg et al. |
| 2003/0212419 A1 | 11/2003 | West |
| 2003/0220660 A1 | 11/2003 | Kortenbach et al. |
| 2004/0006351 A1 | 1/2004 | Gannoe et al. |
| 2004/0034357 A1 | 2/2004 | Beane et al. |
| 2004/0044364 A1 | 3/2004 | DeVries et al. |
| 2004/0082963 A1 | 4/2004 | Gannoe et al. |
| 2004/0092892 A1 | 5/2004 | Kagan |
| 2004/0107004 A1 | 6/2004 | Levine et al. |
| 2004/0143342 A1 | 7/2004 | Stack et al. |
| 2004/0254622 A1 | 12/2004 | Shadduck |
| 2004/0260317 A1 | 12/2004 | Bloom et al. |
| 2004/0260319 A1 | 12/2004 | Egle |
| 2004/0260393 A1 | 12/2004 | Randert et al. |
| 2005/0021061 A1 | 1/2005 | Dennis |
| 2005/0085829 A1 | 4/2005 | Kraemer et al. |
| 2005/0096750 A1 | 5/2005 | Kagan et al. |
| 2005/0120746 A1* | 6/2005 | Winston .......... A44C 9/02 63/38 |
| 2005/0197715 A1 | 9/2005 | Kugler et al. |
| 2005/0251181 A1 | 11/2005 | Bachmann |
| 2005/0251182 A1 | 11/2005 | Bachmann |
| 2005/0283235 A1 | 12/2005 | Kugler et al. |
| 2006/0200179 A1 | 9/2006 | Barker et al. |
| 2006/0241748 A1 | 10/2006 | Lee et al. |
| 2006/0252982 A1 | 11/2006 | Hassler et al. |
| 2006/0252983 A1 | 11/2006 | Lembo et al. |
| 2006/0252984 A1 | 11/2006 | Randert et al. |
| 2006/0276684 A1 | 12/2006 | Speziali |
| 2006/0276812 A1 | 12/2006 | Hill et al. |
| 2007/0004963 A1 | 1/2007 | Benchetrit |
| 2007/0015954 A1 | 1/2007 | Dlugos |
| 2007/0016231 A1 | 1/2007 | Jambor et al. |
| 2007/0021761 A1 | 1/2007 | Phillips |
| 2007/0027356 A1 | 2/2007 | Ortiz |
| 2007/0027357 A1 | 2/2007 | Bertolero et al. |
| 2007/0043256 A1 | 2/2007 | Banik |
| 2007/0073099 A1 | 3/2007 | Forsell |
| 2007/0078296 A1 | 4/2007 | Sabri |
| 2007/0167672 A1 | 7/2007 | Dlugos et al. |
| 2007/0208360 A1 | 9/2007 | Demarais et al. |
| 2007/0213751 A1 | 9/2007 | Scirica et al. |
| 2007/0249894 A1 | 10/2007 | Nicholson |
| 2007/0250087 A1 | 10/2007 | Makower et al. |
| 2008/0027469 A1 | 1/2008 | Bachmann |
| 2008/0083413 A1 | 4/2008 | Forsell |
| 2008/0146869 A1 | 6/2008 | Chow et al. |
| 2008/0161875 A1 | 7/2008 | Stone |
| 2008/0177292 A1 | 7/2008 | Jacobs et al. |
| 2008/0183196 A1 | 7/2008 | Jarsaillon et al. |
| 2008/0287975 A1 | 11/2008 | Weaner et al. |
| 2009/0043356 A1 | 2/2009 | Longhini et al. |
| 2009/0054950 A1 | 2/2009 | Stephens |
| 2009/0062824 A1 | 3/2009 | Berg et al. |
| 2009/0062825 A1 | 3/2009 | Pool et al. |
| 2009/0062826 A1 | 3/2009 | Steffen |
| 2009/0082793 A1 | 3/2009 | Birk |
| 2009/0125102 A1 | 5/2009 | Cartledge et al. |
| 2009/0157107 A1 | 6/2009 | Kierath et al. |
| 2009/0171378 A1 | 7/2009 | Coe et al. |
| 2009/0198261 A1 | 8/2009 | Schweikert |
| 2009/0202387 A1 | 8/2009 | Dlugos et al. |
| 2009/0216255 A1 | 8/2009 | Coe et al. |
| 2009/0216256 A1 | 8/2009 | Nicholson |
| 2009/0228028 A1 | 9/2009 | Coe et al. |
| 2009/0240268 A1 | 9/2009 | Kassab et al. |
| 2009/0240269 A1 | 9/2009 | Denis |
| 2009/0306462 A1 | 12/2009 | Lechner |
| 2009/0306463 A1 | 12/2009 | Mouton et al. |
| 2010/0030014 A1 | 2/2010 | Ferrazzi |
| 2010/0099945 A1 | 4/2010 | Birk et al. |
| 2010/0114131 A1 | 5/2010 | Rotunda |
| 2010/0179376 A1 | 7/2010 | Kassab et al. |
| 2010/0185049 A1 | 7/2010 | Birk et al. |
| 2010/0191265 A1 | 7/2010 | Lau et al. |
| 2010/0217071 A1 | 8/2010 | Ricol |
| 2010/0280310 A1 | 11/2010 | Raven |
| 2010/0312046 A1 | 12/2010 | Lau et al. |
| 2010/0324359 A1 | 12/2010 | Birk |
| 2011/0034760 A1 | 2/2011 | Brynelsen et al. |
| 2011/0034761 A1 | 2/2011 | Ricol |
| 2011/0034762 A1 | 2/2011 | Paganon |
| 2011/0040141 A1 | 2/2011 | Bachmann et al. |
| 2011/0054248 A1 | 3/2011 | Birk et al. |
| 2011/0071341 A1 | 3/2011 | Dlugos et al. |
| 2011/0071557 A1 | 3/2011 | Dlugos et al. |
| 2011/0071558 A1 | 3/2011 | Dlugos et al. |
| 2011/0152608 A1 | 6/2011 | Bachmann et al. |
| 2011/0152901 A1 | 6/2011 | Woodruff et al. |
| 2012/0150214 A1 | 6/2012 | Kugler et al. |

FOREIGN PATENT DOCUMENTS

| | | |
|---|---|---|
| EP | 0341039 | 11/1989 |
| JP | S53-107507 | 8/1978 |
| JP | S58-008323 | 1/1983 |
| JP | S59-069744 | 4/1984 |
| JP | H04-117905 | 10/1992 |
| WO | WO 93/19702 | 10/1993 |
| WO | WO 98/44965 | 10/1998 |
| WO | WO 00/54835 | 9/2000 |
| WO | WO 00/59398 | 10/2000 |
| WO | WO 01/08717 | 2/2001 |
| WO | WO 01/47431 | 7/2001 |
| WO | WO 02/094132 | 11/2002 |
| WO | WO 04/004544 | 1/2004 |
| WO | WO 2009/005634 | 1/2009 |

OTHER PUBLICATIONS

Alksne, J. et al., "Iron-acrylic compound for stereotaxic aneurysm thrombosis," J. Neurosurg., vol. 47, pp. 137-141 (Aug. 1977).

Branton, S.A. et al., "Surgical Treatment of Gastroesophageal Reflux Disease," The Esophagus, Lippincott Williams & Wilkins, Castell, D.O. et al., Third Edition, 1999, pp. 511-525.

Evangelisto, Mary, "How Do Some Spell Relief? S-u-r-g-e-r-y," Today's Surgical Nurse, vol. 19, No. 1, 1997, pp. 22-28.

Gruneburger, A.D. et al., "Entwicklung eines magnetischen Urethralverschlusses—eine tier-experimentelle Studie," Zentralbl Gynakol, vol. 115, pp. 328-331 (1993).

Gruneburger, A.D., "Entwicklung eines magnetischen Urethralverschlusses and erste klinische Erfahrungen," Urologe A, vol. 26, pp. 106-111 (1987).

Gruneburger, A.D., "Klinische Erfahrungen mit einem magnetischen Harnrohrenverschluß," Geburtsch. u. Frauenheilk., vol. 50, pp. 150-154 (1990).

(56) References Cited

OTHER PUBLICATIONS

Gruneburger, A.D., "Modifikation der Anwendung der Magnetschale des Harnrohrenverschlusses bei Rezidiv-Inkontinenz," Geburtsch. u. Frauenheilk., vol. 51, pp. 850-852 (1991).
Kahrilas, P.J. et al., "Hiatus Hernia," The Esophagus Lippincott Williams & Wilkins, Castell, D.O. et al., Third Edition, 1999, pp. 381-396.
MUSC Digestive Disease Center, "Digestive Problems: Esophagus—GERD," Oct. 13, 2003, accessed Mar. 3, 2004 at www.ddc.musc.edu/ddc_pub/digestiveProbs/diseases/esophagus/GERD.htm.
MUSC Digestive Disease Center, "Patient Information: Laparoscopic Surgeries—Fundoplication," Oct. 13, 2003, accessed Mar. 3, 2004 at www.ddc.musc.edu/ddc_pub/patientInfo/surgeries/laparoscopic/ fundoplication.htm.
Sayre, J.T., et al., "Current Experiences with the Management of Paraesophageal Hernias," Connecticut Medicine, vol. 44, No. 4, Apr. 1980, pp. 197-203.
Shigley et al., Mechanical Engineering Design, Fifth Edition, 1989, McGraw-Hill, Inc., New York, pp. 58-60.
European Examination Report dated Dec. 28, 2010 for Application No. EP 05775698.3, 4 pgs.
European Communication, Intention to Grant, dated Dec. 5, 2014 for Application No. EP 05775698.3, 58 pgs.
European Search Report and Written Opinion dated Mar. 7, 2012 for Application No. EP 11192074.0, 6 pgs.
European Examination Report dated Jul. 21, 2015 for Application No. EP 11192074.0, 4 pgs.
European Examination Report dated Nov. 30, 2017 for Application No. EP 11192074.0, 3 pgs.
European Communication, Intention to Grant, dated May 3, 2018 for Application No. EP 11192074.0, 48 pgs.
European Search Report and Written Opinion dated Mar. 7, 2012 for Application No. EP 11192082.3, 5 pgs.
European Examination Report dated Jul. 21, 2015 for Application No. EP 11192082.3, 3 pgs.
International Search Report and Written Opinion dated Nov. 2, 2004 for Application No. PCT/US2004/002386, 15 pgs.
International Search Report and Written Opinion dated Jul. 4, 2005 for Application No. PCT/US2005/005826, 12 pgs.
International Search Report and Written Opinion dated Dec. 29, 2005 for Application No. PCT/US2005/026469, 11 pgs.
Japanese Office Action, Notification of Reasons for Refusal, dated Mar. 23, 2011 for Application No. JP 2007-524843, 3 pgs.
Japanese Office Action, Notification of Reasons for Refusal, dated Dec. 2, 2011 for Application No. JP 2007-524843, 2 pgs.
Japanese Office Action, Decision to Grant a Patent, dated Mar. 2, 2012 for Application No. JP 2007-524843, 3 pgs.
U.S. Appl. No. 10/732,693, filed Dec. 9, 2003, by Berg.
U.S. Appl. No. 60/614,835, filed Sep. 30, 2004.
U.S. Appl. No. 60/653,966, filed Feb. 17, 2005.
Extended European Search Report and Written Opinion dated Feb. 12, 2019 for Application No. 18190008.5, 6 pages.

\* cited by examiner

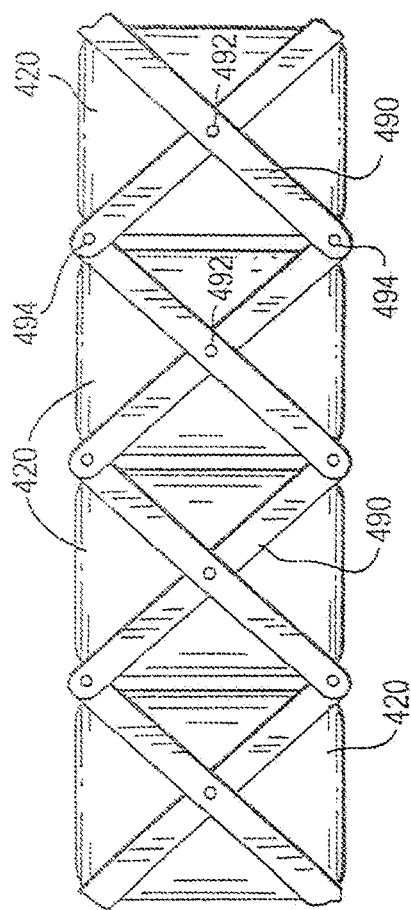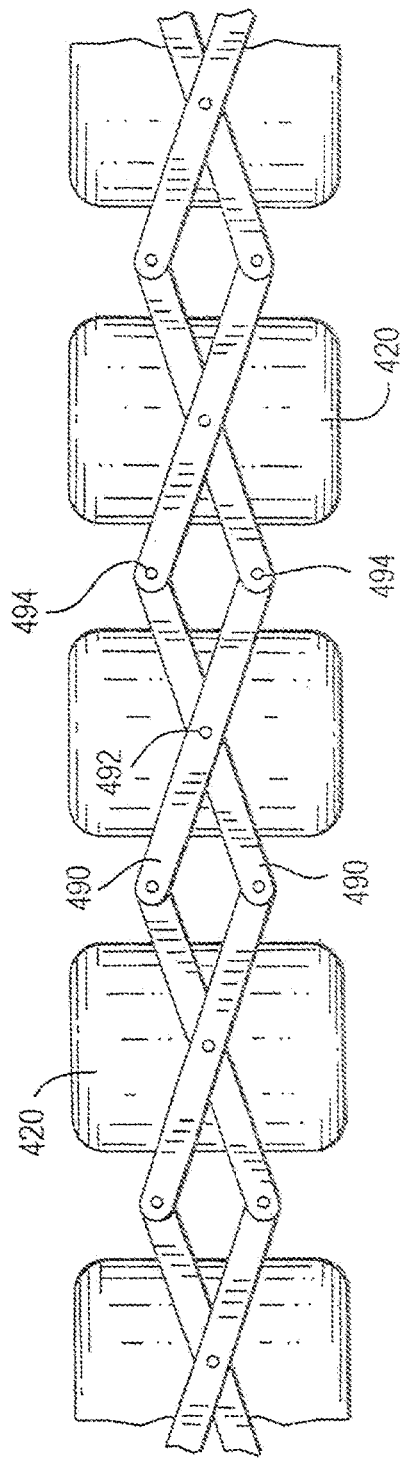

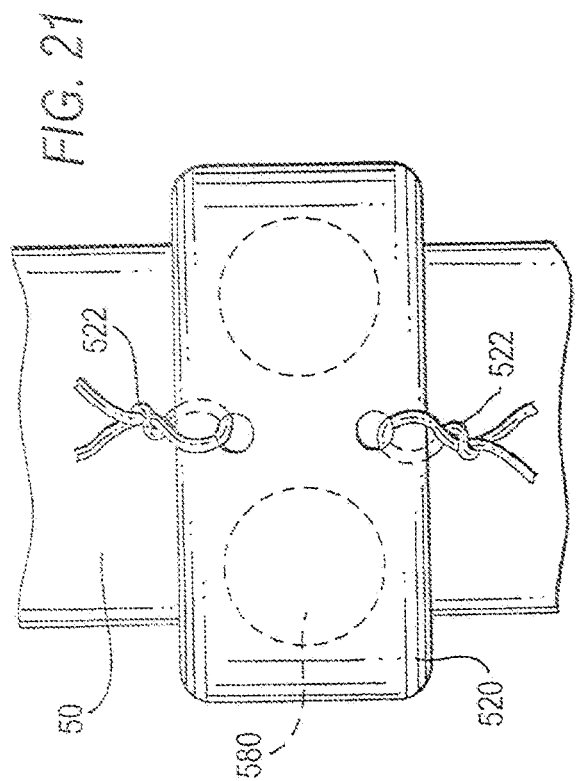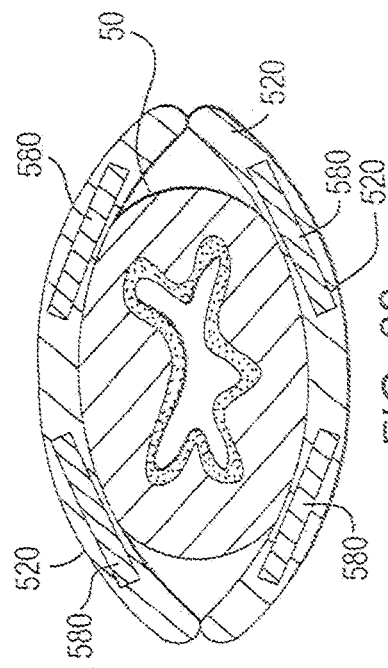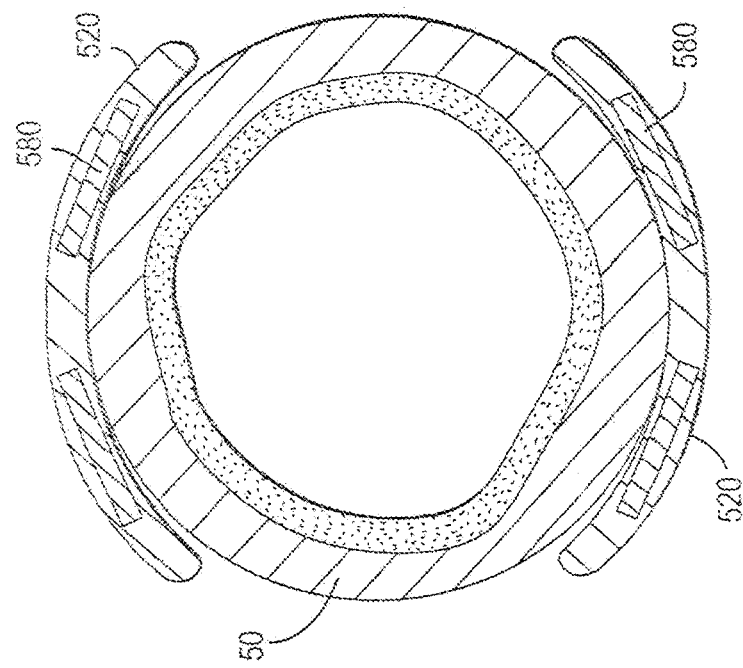

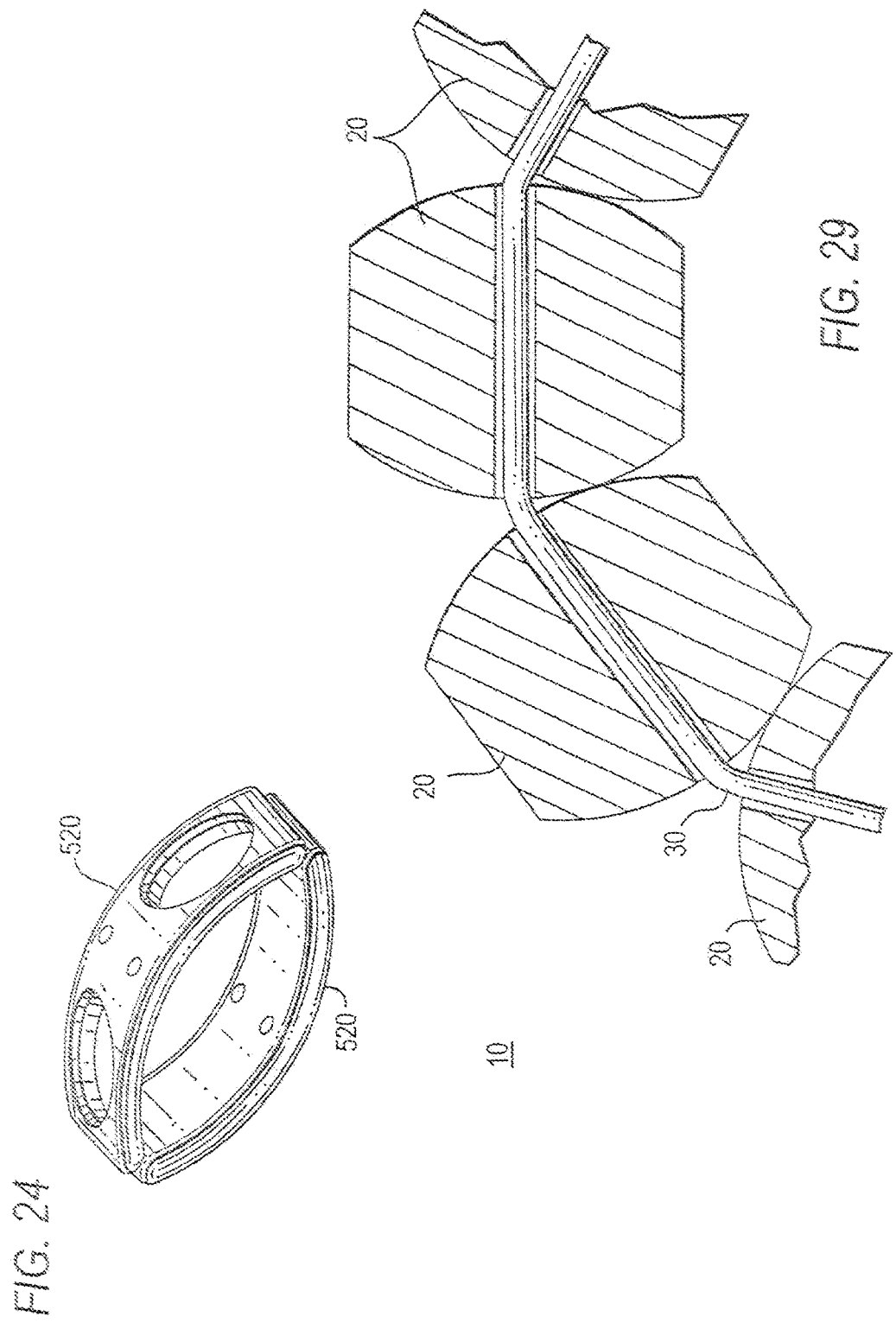

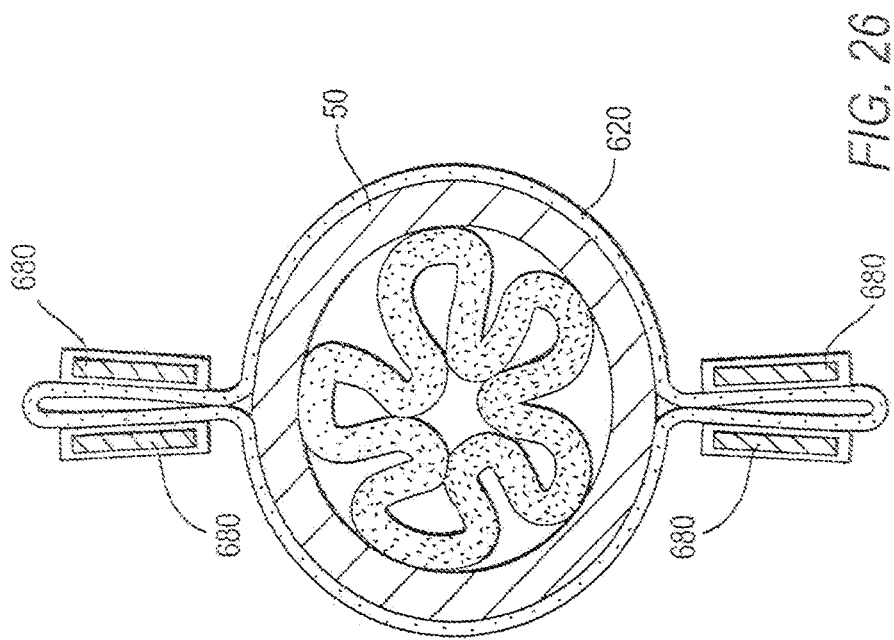
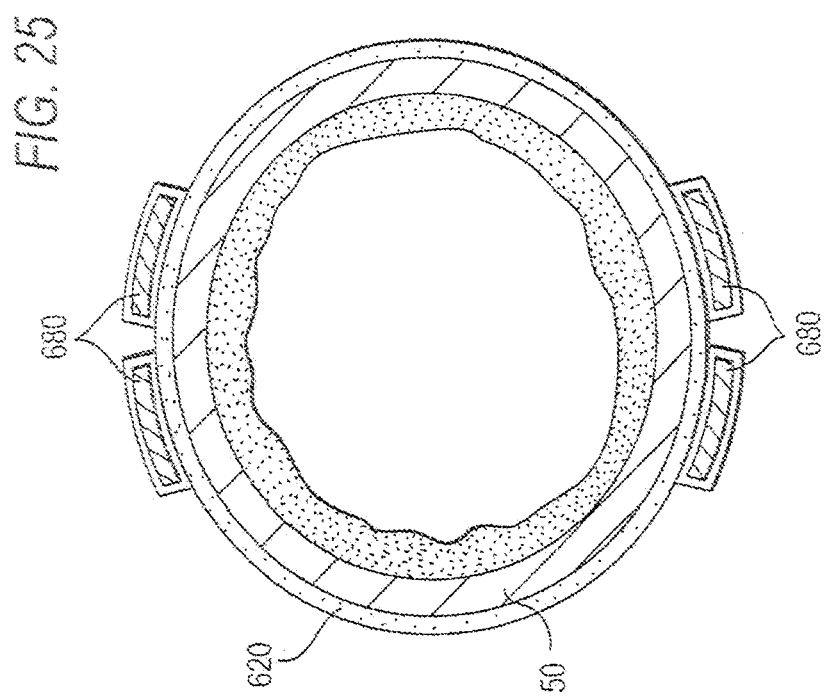

METHODS AND APPARATUS FOR TREATING BODY TISSUE SPHINCTERS AND THE LIKE

This application is a continuation of U.S. patent application Ser. No. 14/445,723, entitled "Methods and Apparatus for Treating Body Tissue Sphincters and the Like," filed Jul. 29, 2014, issued as U.S. Pat. No. 10,398,440 on Sep. 3, 2019, which is a division of U.S. patent application Ser. No. 13/403,441, entitled "Methods and Apparatus for Treating Body Tissue Sphincters and the Like," filed Feb. 23, 2012, now abandoned, which is a divisional of U.S. patent application Ser. No. 12/610,633, entitled "Methods and Apparatus for Treating Body Tissue Sphincters and the Like, filed Nov. 2, 2009, issued as U.S. Pat. No. 8,187,164 on May 29, 2012, which is a continuation of Ser. No. 11/147,801, entitled "Methods and Apparatus for Treating Body Tissue Sphincters and the Like, filed Jun. 7, 2005, issued as U.S. Pat. No. 7,695,427 on Apr. 13, 2010, which claims the benefit of U.S. provisional patent applications 60/599,333, filed Aug. 5, 2004; 60/614,835, filed Sep. 30, 2004; and 60/653,966, filed Feb. 17, 2005.

BACKGROUND OF THE INVENTION

This invention relates to medical implants for improving or modifying the performance of tissue structures in a patient's body such as a sphincter, a tubular conduit, or an organ. An illustrative use of the invention is improving the performance of a patient's lower esophageal sphincter ("LES") as a treatment for gastro-esophageal reflux disorder or disease ("GERD"). However, this is only an example of how the invention may be used, and many other uses will be readily apparent to those skilled in the art. To list just a few further examples, the invention may be applied to other sphincters in the body such as sphincters in the urinary tract and elsewhere in the digestive tract. The apparatus of the invention may be used around the stomach as part of a treatment for obesity.

A common cause of GERD is inadequate functioning of the LES. The LES (and perhaps some associated tissue structures) normally keeps the lower part of the esophagus closed in order to prevent stomach contents from entering the esophagus. The LES opens during swallowing to allow whatever is being swallowed to pass from the esophagus into the stomach. The LES also opens to allow excess pressure in the stomach to escape via the esophagus. However, normal stomach pressure is substantially resisted by a normally functioning LES to keep the contents of the stomach from entering the esophagus. In a patient with GERD the cause is frequently an LES that has lost its ability (strength or "tone") to resist normal stomach pressure and prevent stomach contents from coming back into the esophagus. This can cause discomfort ("heartburn"), and if left untreated, can cause damage to the esophagus that can lead to very serious adverse consequences for the patient.

It has been proposed to implant magnets in a GERD patient to improve the strength or tone of the patient's LES. For example, two magnets may be implanted in the esophagus on respective opposite sides of the esophageal lumen at or near the LES. Magnetic attraction between the magnets helps to hold the esophagus closed (except during swallowing or excess stomach pressure venting) and thereby reduces or eliminates the reflux of GERD. In following this approach, it would be desirable to avoid subjecting tissue to long-term, direct pressure from the magnets, such as when tissue between two mutually attracting magnets or magnetic structures is the only thing keeping the magnets or magnetic structures apart. Such pressure can interfere with blood flow to the tissue between the magnets or magnetic structures, which can be unhealthy for that tissue. For example, tissue death (necrosis) can result.

SUMMARY OF THE INVENTION

In accordance with the invention, a medical implant includes plural bodies, adjacent ones of which are resiliently attracted to one another (e.g., by magnetism, spring force, or the like). The bodies can be disposed in an array (e.g., an annular array) around a body tissue structure to be treated. The structure of the implant maintains an open area inside the array of at least a predetermined non-zero minimum size. Tissue passing through that area may be subjected to some residual pressure, e.g., of the kind and in an amount that improves the tone of a sphincter that is part of that tissue. But no part of the tissue is exposed to pressure of the kind that would be unhealthy for the tissue. If a normal body function (e.g., swallowing) causes the tissue structure passing through the array of bodies that make up the implant or prosthesis to need to expand, those bodies can move resiliently apart to allow such enlargement of the tissue structure. Thereafter, the bodies of the prosthesis move resiliently back toward one another again to help the tissue structure contract to its first-mentioned condition. However, this contraction of the prosthesis is limited by the prosthesis itself to always leave open at least the above-mentioned non-zero minimum area bounded by the prosthesis. The contracting prosthesis may not always reach the above-mentioned limit, if the prosthesis is sized or designed to apply some residual pressure to the tissue. But if that is the case, the residual pressure is small enough (e.g., it is the result of a relatively small force distributed over a relatively large area of tissue) so that it is not a problem for the tissue even if applied long-term.

Other aspects of the invention relate to methods for implanting a prosthesis in a patient in accordance with the invention. For example, an implant in accordance with the invention may be introduced into the patient in a substantially linear array. The array may be wrapped around the outside of the target body tissue structure. Opposite ends of the array may be joined to one another to form a closed loop around the target body tissue structure. These steps may be performed in any of a number of ways. For example, the implanting may be done surgically. As another example, the implanting may be done laparoscopically. As still another example, the prosthesis may be delivered into the patient via a body conduit of the patient, may then exit from that conduit at a location interior to the patient, and may then be implanted at the intended site using instrumentation that accompanies or follows the prosthesis into the patient via the conduit and out of that conduit at the interior location. As a specific example of the last-mentioned possibility, the prosthesis may be delivered into the patient in a linear condition via the patient's mouth and esophagus and into the stomach. The prosthesis may then exit through a temporary aperture in the side wall of the stomach and thereby enter the extra-luminal space. The prosthesis may then be secured around the external esophagus or upper stomach.

Further features of the invention, its nature and various advantages will be more apparent from the accompanying drawings and the following detailed description of the preferred embodiments.

BRIEF DESCRIPTION OF THE DRAWINGS

FIG. 19 is a simplified elevational view of a representative portion of yet another illustrative embodiment of prosthetic implant apparatus in accordance with the invention.

FIG. 20 is similar to FIG. 19, but shows another operating condition of the apparatus.

FIG. 21 is a simplified elevational view showing use of still another illustrative embodiment of prosthetic implant apparatus in accordance with the invention.

FIG. 22 is a simplified cross sectional view of what is shown in FIG. 21.

FIG. 23 is similar to FIG. 22, but shows another operating condition of the apparatus.

FIG. 24 is a simplified perspective of portions of prosthetic implant apparatus like that shown in FIGS. 21-23.

FIG. 25 is similar to FIG. 23 for yet another illustrative embodiment of prosthetic implant apparatus in accordance with the invention.

FIG. 26 is similar to FIG. 25, but shows another operating condition of the apparatus.

FIG. 29 is generally similar to FIG. 5 for another illustrative embodiment of the invention.

DETAILED DESCRIPTION

Figure 1:
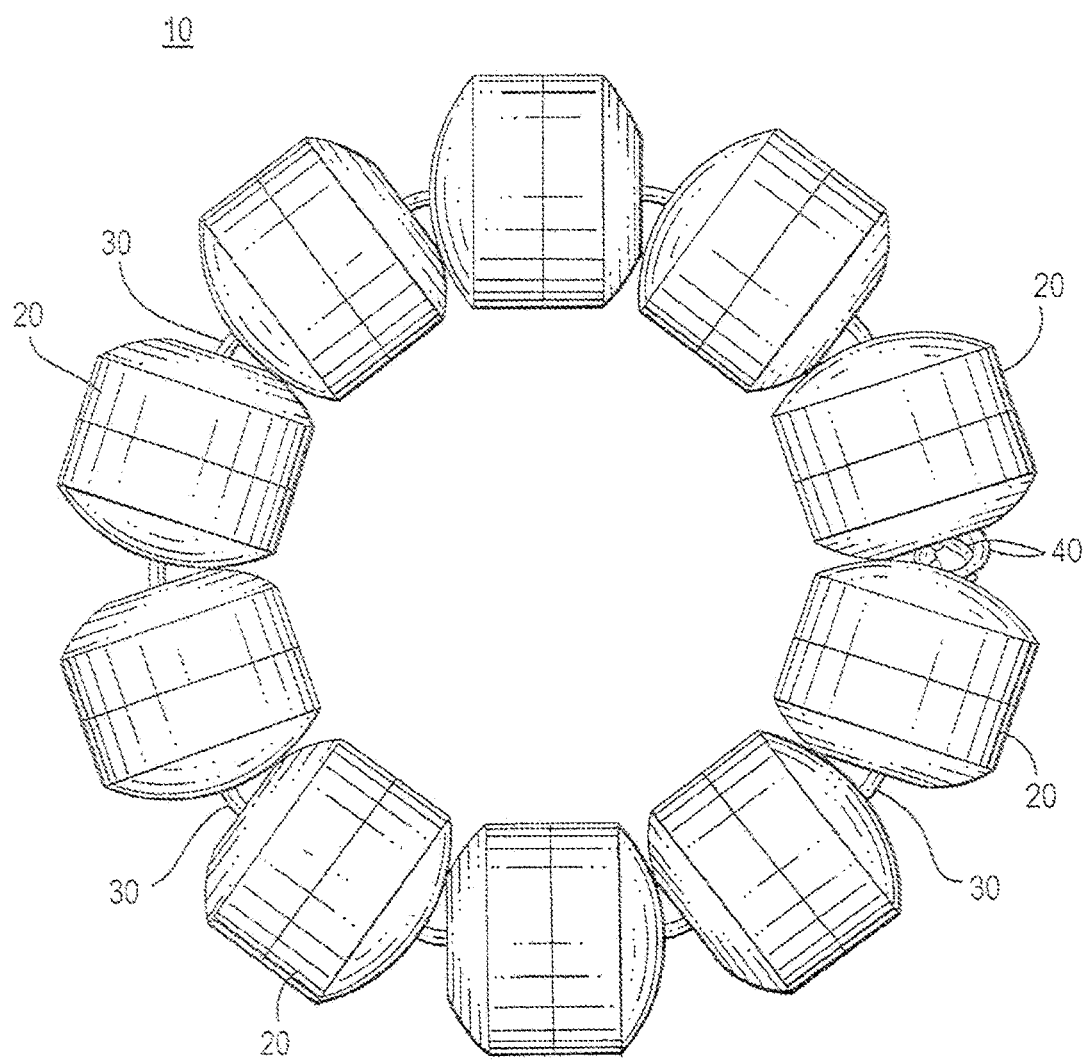
FIG. 1 is a simplified elevational view of an illustrative embodiment of prosthetic implant apparatus in accordance with the invention.
Figure 2:
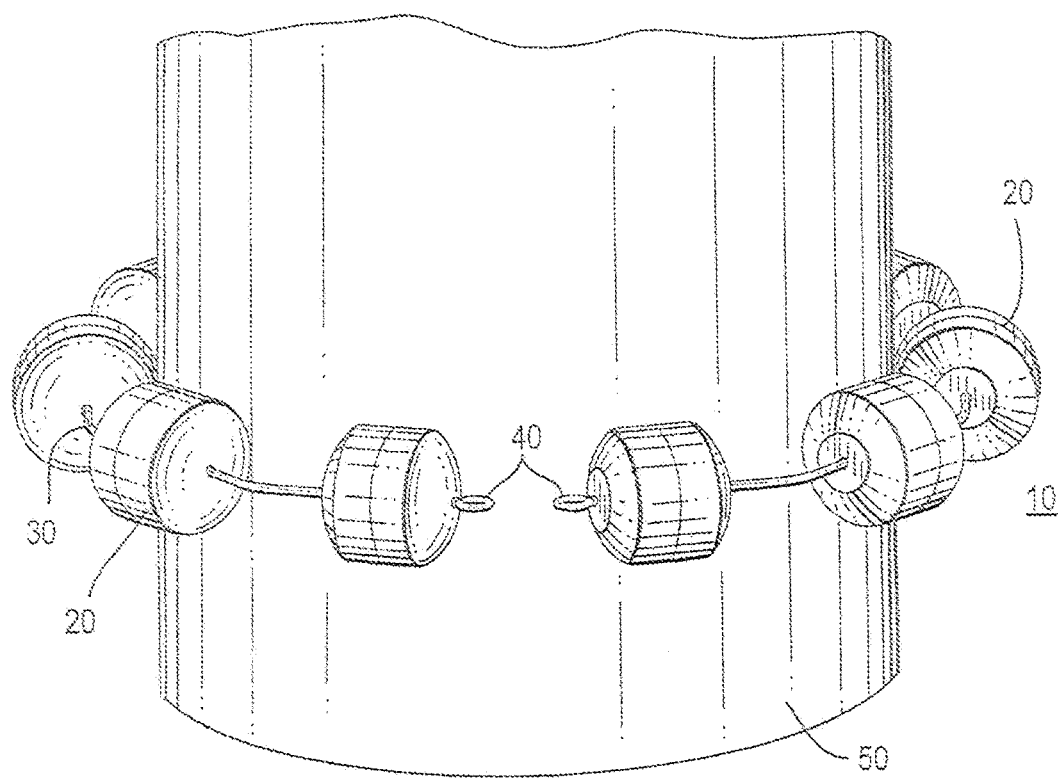
FIG. 2 is a simplified perspective view of apparatus of the type shown in FIG. 1 implanted and functioning in a patient in accordance with the invention.
Figure 4:
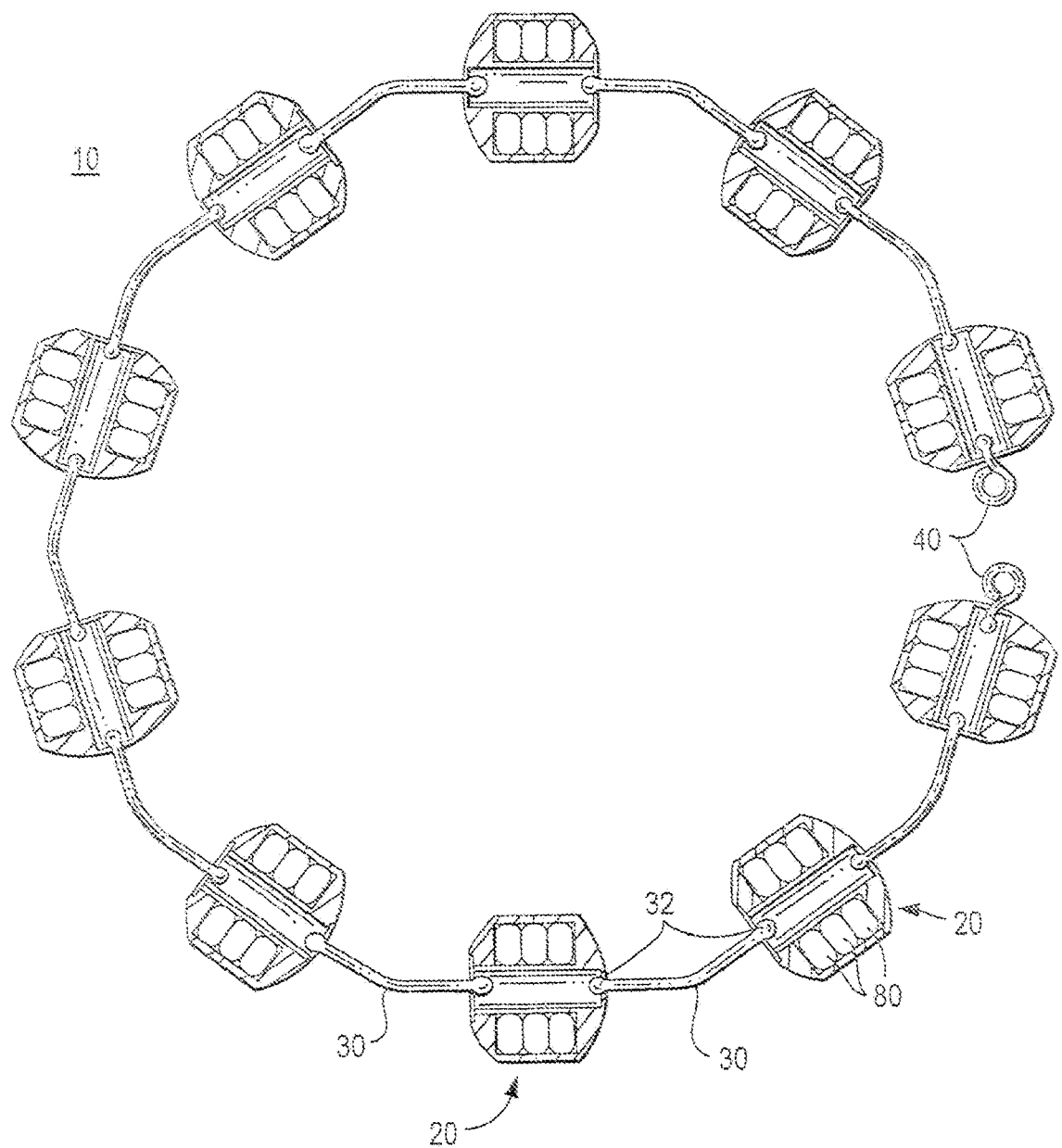
FIG. 4 is similar to FIG. 1, but shows another operating condition of the apparatus.

As shown in FIG. 1, an illustrative embodiment of apparatus 10 in accordance with the invention includes a plurality of substantially cylindrical bodies or "beads" 20. Beads 20 can be formed into a closed loop with an open interior as shown in FIG. 1. Beads 20 are strung together by links 30. In general, each bead 20 has a link 30 to each of the immediately adjacent beads on each side of the first-mentioned bead. The possible exception to this is for the linkage between the two right-most beads in FIG. 1. Each of these beads has a link eyelet 40 extending outwardly from the bead toward the other of these beads. Link eyelets 40 may initially be separate from one another (e.g., as shown in FIG. 2 or FIG. 4). This allows apparatus 10 to (at least initially) not form a closed loop, which non-loop condition may be helpful in initially implanting the apparatus in a patient. If and when desired, link eyelets 40 may be connected to one another (e.g., by tying them together with a strand of suture material). For example, FIG. 2 shows apparatus 10 implanted annularly and coaxially around the outside of a patient's esophagus 50. Although FIG. 2 does not show a connection between link eyelets 40, it will be apparent that such a connection can be made (e.g., with suture material). As will be seen, links 30/40 are important to controlling the position of each bead 20 and for allowing diameter increases of the prosthesis.

Each bead 20 in apparatus 10 is resiliently attracted to the adjacent beads in the string or loop. This resilient attraction may be provided by means such as magnetic force, spring force, or the like. Use of magnetic force will be described first. Other examples will be described later.

Figure 3:
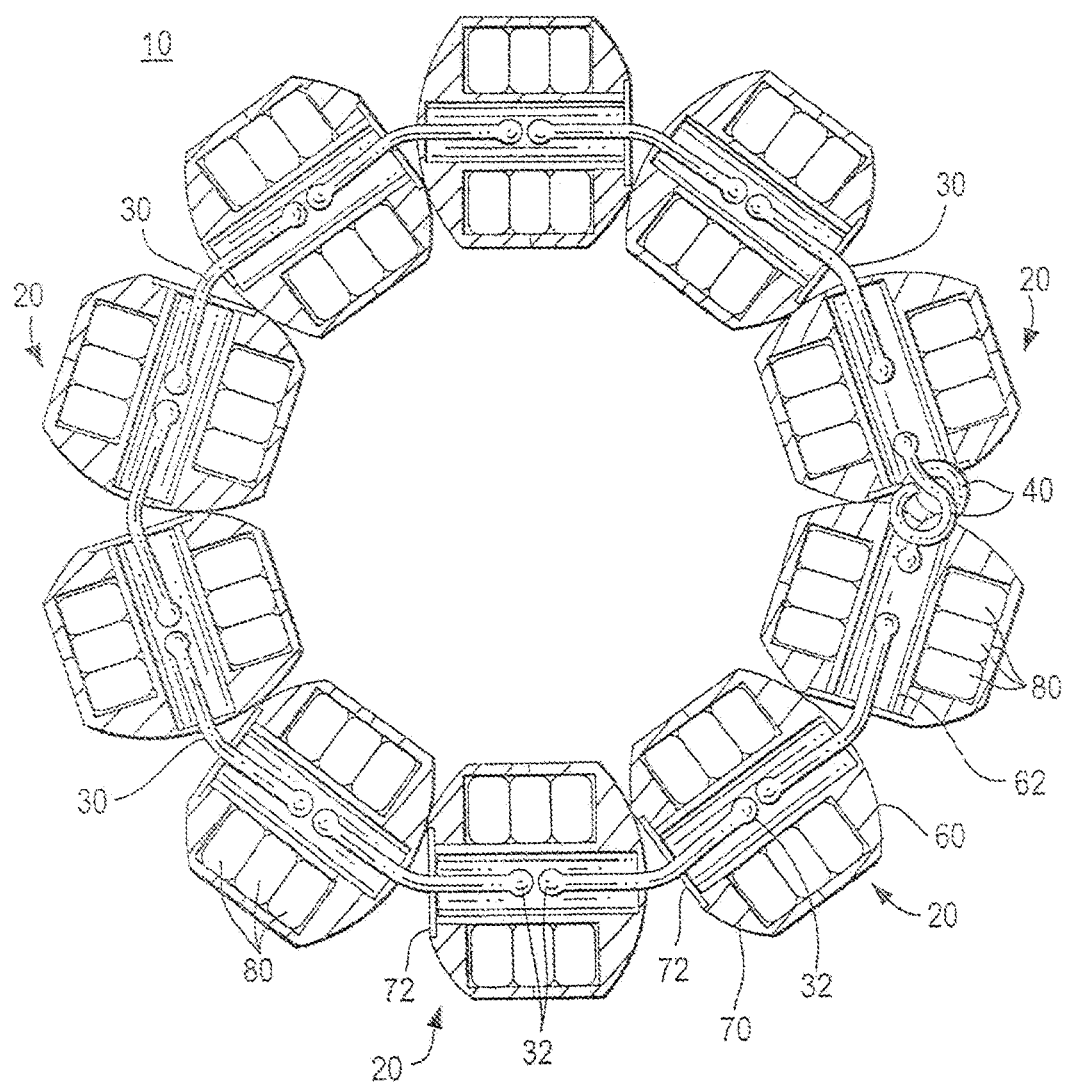
FIG. 3 is a simplified sectional view of apparatus of the type shown in FIG. 1.
Figure 5:
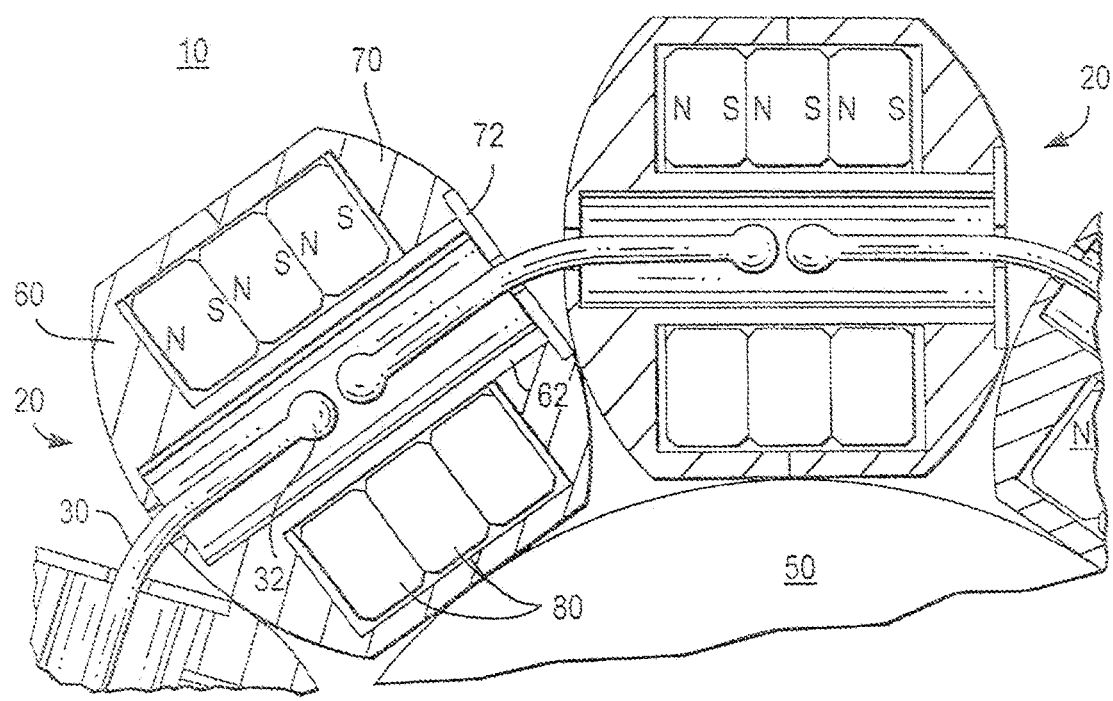
FIG. 5 is an enlargement of a representative portion of what is shown in FIG. 3.

FIGS. 3-5 show an example in which magnetic force is used to attract adjacent beads 20 to one another. Each bead 20 includes two mating housing components 60 and 70. Each housing component 60 or 70 is basically cup-shaped. Each housing component 60 has a hollow post 62 standing up from the center of its bottom. The part of each post 62 that is most remote from the remainder of cup 60 extends into an aperture in the bottom of the associated cup 70. The lips of the cups 60 and 70 that form a bead 20 abut one another annularly around the bead. Thus the interiors of the cups 60 and 70 of a bead 20 form a hollow annular space inside the bead and concentrically around the post 62 inside the bead. One or more toroidal permanent magnets 80 are concentrically disposed about post 62 in this space. Magnets 80 are magnetically polarized so that the magnets in adjacent beads 20 in the string or loop magnetically attract one another. (See FIG. 5 in which the polarity of each magnet 80 is indicated by the letters N and S.) This magnetic attraction resiliently attracts adjacent beads in the string or loop toward one another.

The hollow interior of each post 62 is large enough to easily and loosely accommodate end portions of two links 30 (or end portions of one link 30 and one link eyelet 40). (Because for this purpose link eyelets 40 are substantially similar to links 30, it will not be necessary to separately mention eyelets 40 again in this immediate discussion. It will be understood that they are subsumed in the discussion of links 30.) In each bead 20 one of the associated links 30 extends out of an aperture in the bottom of cup 60. This aperture is large enough to allow the main length of the link 30 to pass freely through the aperture, but it is not large enough to allow an enlarged stop 32 at the end of the link to pass through the aperture. The other link 30 associated with each bead 20 extends out of an aperture in the center of a washer-like cap 72 that is used to substantially close an aperture in the bottom of cup 70 and the otherwise open end of the hollow in post 62. Again, the aperture in cap 72 is large enough to allow the main length of the associated link 30 to pass freely through, but it is not large enough to allow the enlarged stop 32 at the end of the link to pass.

The various components of apparatus 10 can be assembled (during manufacture) as follows. Each link 30 can be initially provided with only one enlarged end stop 32. The other end of a link 30 can be passed successively through the aperture in the bottom of a cup 60 (not yet attached to a cup 70) and the aperture in a washer-like cap 72 (also not yet attached to a cup 70). An enlarged end stop 32 can be formed on the other end of the link 30. Magnets 80 can be placed in the cup 60. A cup 70 can be attached to the cup 60. A washer-like cap 72 can be attached to the cup 70.

Magnets 80 do not need to be biocompatible because the magnets can be completely sealed inside beads 20. The parts of apparatus 10 that will be exposed to a patient's body are preferably biocompatible. These components are cups 60 and 70 (including posts 62), washer-like caps 72, and links 30/40. An example of a biocompatible material that is suitable for these components is titanium, but many other suitable metallic and non-metallic materials are known to those skilled in art and can be used if and as desired. Assuming that one or more metals are used for components 30, 40, 60, 62, 70, and 72, enlarged end stops 32 may be formed as weld balls, annular hermetic welds may be formed between the abutting lips of cups 60 and 70, a similar annular hermetic weld may be formed between mating components 62 and 70, and spot welds may be used to secure washer-like caps 72 to the associated cups 70. Hermetic sealing of this last connection is not required because of the hermetic sealing between components 62 and 70. Alternatively, the mating between components 62 and 70 could be left unsealed, and a seal weld could be used between component 72, on the one hand, and components 62 and 70, on the other hand.

Note that the ends of each cylindrical bead 20 are preferably approximately spherical. Note also that links 30 may be somewhat bent laterally along their lengths. Features such as these help the structure form a closed loop that can resiliently enlarge and contract without mechanical interference (other than the intended ultimate limits on both enlargement and contraction as will now be described).

As has been mentioned, the magnets 80 in beads 20 resiliently attract adjacent beads into contact with one another as shown in FIGS. 1, 3, and 5. However, this magnetic attraction between adjacent beads can be overcome, e.g., by sufficiently forceful radial enlargement of a patient's body tissue structure that passes through the interior of a closed loop of the beads. For example, FIG. 2 shows beads 20 separated from one another in the annular direction by temporary radial enlargement of esophagus 50 (e.g., due to swallowing of a bolus of food). FIG. 4 shows the extreme upper limit of annular enlargement of apparatus 10. This enlargement limit is reached when each link 30/40 is pulled as far out of each bead 20 as the enlarged stops 32 on the ends of the links will permit. (It is assumed in this discussion of FIG. 4 that eyelets 40 are attached to one another (e.g., by a suture knot (not shown) between them).) Annular enlargement of apparatus 10 is stopped by attainment of this condition.

At all times that apparatus 10 is annularly enlarged to any degree, it is resiliently urged to return to its fully, annularly contracted condition by the magnetic attraction between beads 20. (Note that apparatus 10 has its lowest force urging contraction when beads 20 are at maximum separation from one another (e.g., as shown in FIGS. 2 and 4).) Annular contraction of apparatus 10 is, however, ultimately limited by each bead 20 coming into contact with the adjacent beads in the string or loop. This maximally contracted condition of apparatus 10 is shown, for example, in FIGS. 1, 3, and 5. (Note that apparatus 10 has its highest force urging contraction when beads 20 are closest together as shown in FIGS. 1, 3, and 5.) When each bead 20 is in contact with the adjacent beads as shown in these FIGS., the apparatus itself stops or prevents any further annular contraction of the apparatus. The structure is completely stable in this condition. Beyond this point the apparatus applies no additional pressure to the patient's body tissue structure that passes through the interior of the apparatus. This self-stopping or self-limiting contraction of the apparatus of the invention can be an important advantage. If the only thing resisting resilient movement of two (or more) bodies toward one another is tissue between the bodies, the continuous pressure of those bodies on the tissue can adversely affect the tissue if that pressure is sufficiently great. For example, it may cause necrosis of the tissue. This cannot happen with embodiments of this invention (like the one being discussed) in which the apparatus itself ultimately absorbs force exerted by components of the apparatus beyond the force that produces maximum annular contraction of the apparatus. The interior of apparatus 10 always remains open as shown in FIG. 1, even if there were no tissue in that interior.

Figure 7:
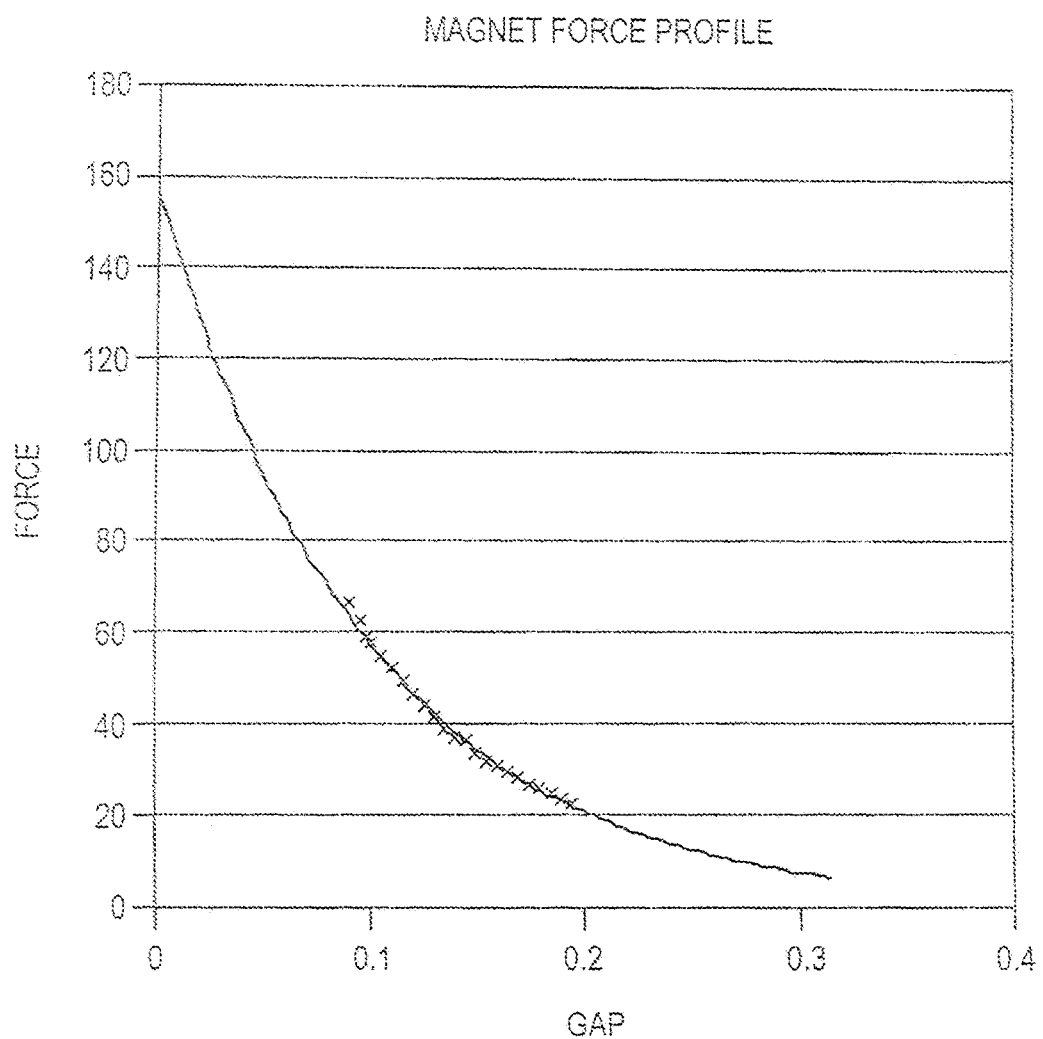
FIG. 7 is a graph that is useful in explaining certain aspects of the invention.
Figure 8:
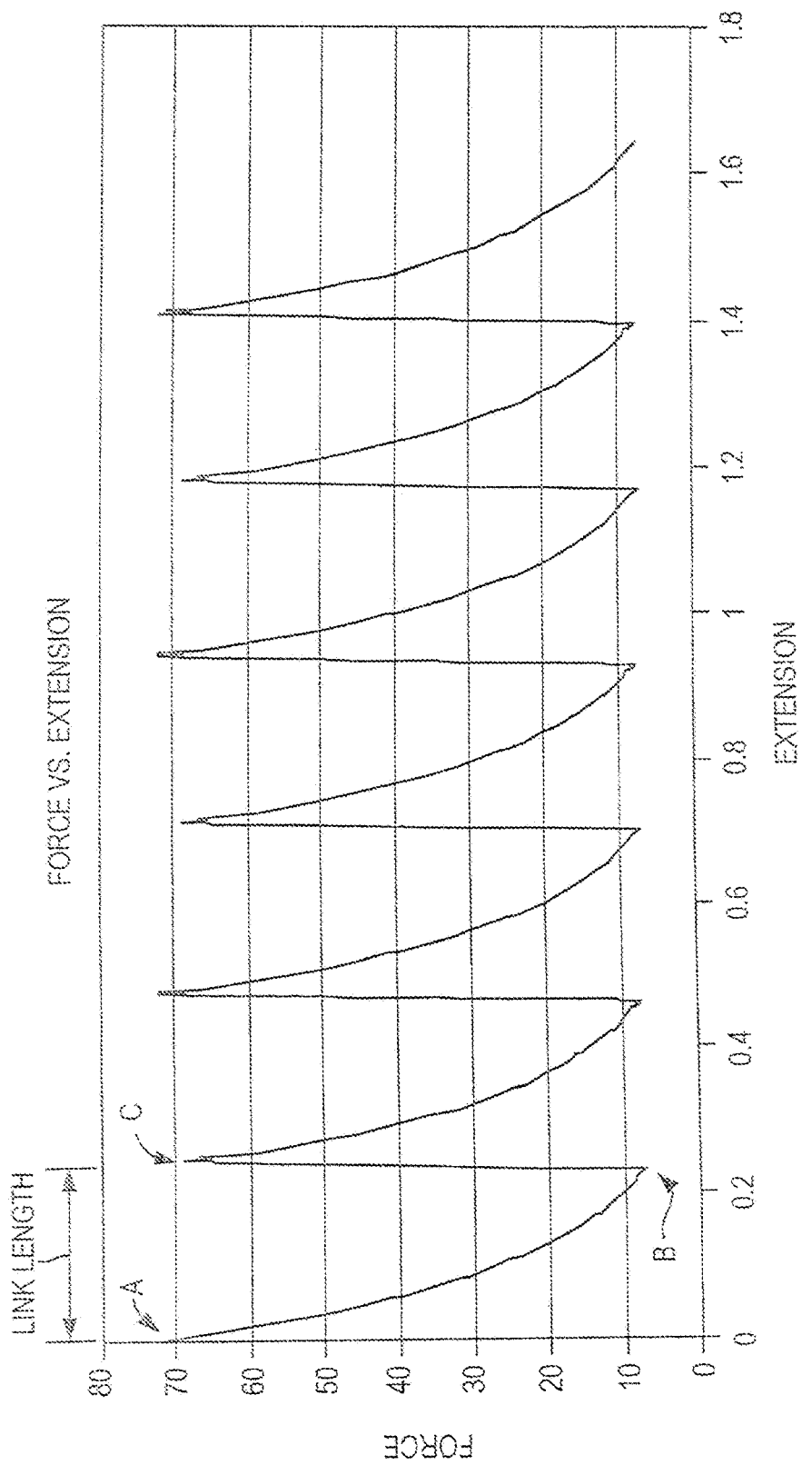
FIG. 8 is another graph that is useful in explaining certain aspects of the invention.

Certain aspects of the behavior of apparatus 10 are illustrated by FIGS. 7 and 8. FIG. 7 is a graph of force versus separation between two bodies that are magnetically attracted to one another. FIG. 7 illustrates the well known fact that as the distance between the two objects increases, the magnetic force attracting them toward one another decreases, and the decrease is an exponential function of the gap or spacing between the bodies.

FIG. 8 shows how the principle of FIG. 7 applies in the case of apparatus like above-described apparatus 10. When apparatus 10 is in its most annularly contracted condition with each of beads 20 in contact with the adjacent beads, the magnetic force holding apparatus 10 in that state of maximum contraction (or zero extension, in the terms employed in FIG. 8) is at a maximum (point A in FIG. 8). If apparatus 10 is then subjected to at least that amount of force tending to annularly enlarge it, two of beads 20 will begin to move apart. Assuming that all of beads 20 have the same magnetic attraction to their neighboring, adjacent beads, it can be a matter of chance which two of the beads begin to separate from one another. As soon as two beads begin to separate, the force required to continue the separation of these two beads drops exponentially, until maximum separation between these two beads is reached at point B in FIG. 8. Note that there is still some resilient, restorative force at point B.

If, beyond the enlargement of apparatus 10 that has occurred when point B is reached, still more enlargement is needed, the force required to initiate such further enlargement returns to approximately the starting force as shown at point C. If at least such further enlargement force is present, two more of beads 20 will begin to separate to provide a further annular enlargement of apparatus 10.

The above-described process of beads 20 separating from one another one after another will continue, following the force and displacement diagram shown in FIG. 8, until the patient's body tissue structure that is inside apparatus 10 has reached a size such that it no longer exerts sufficient enlarging force on the apparatus to cause further enlargement of the apparatus, or until the apparatus has reached its condition of maximum annular enlargement.

Figure 9:
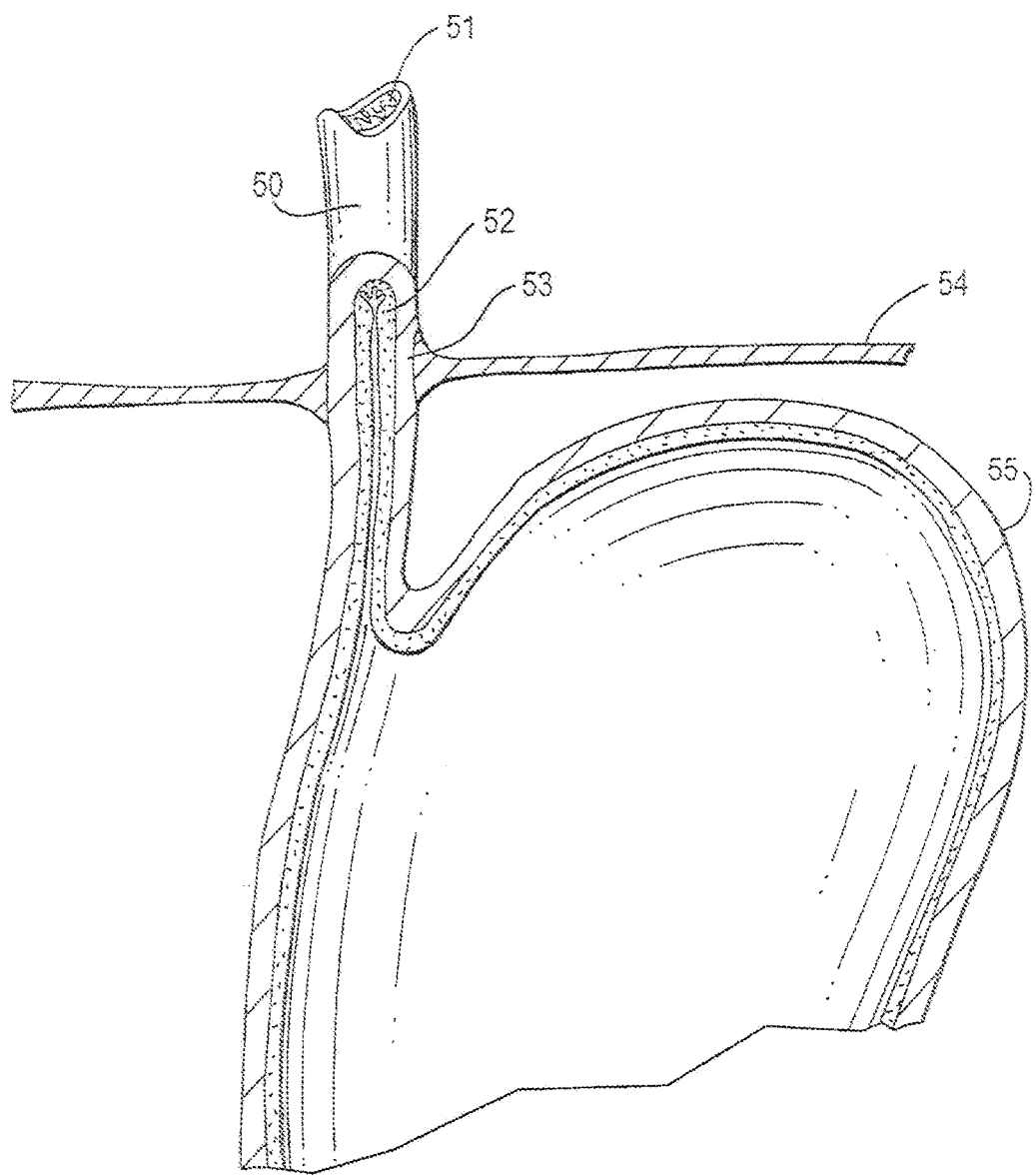
FIG. 9 is a simplified sectional view of a portion of a patient's anatomy.
Figure 10:
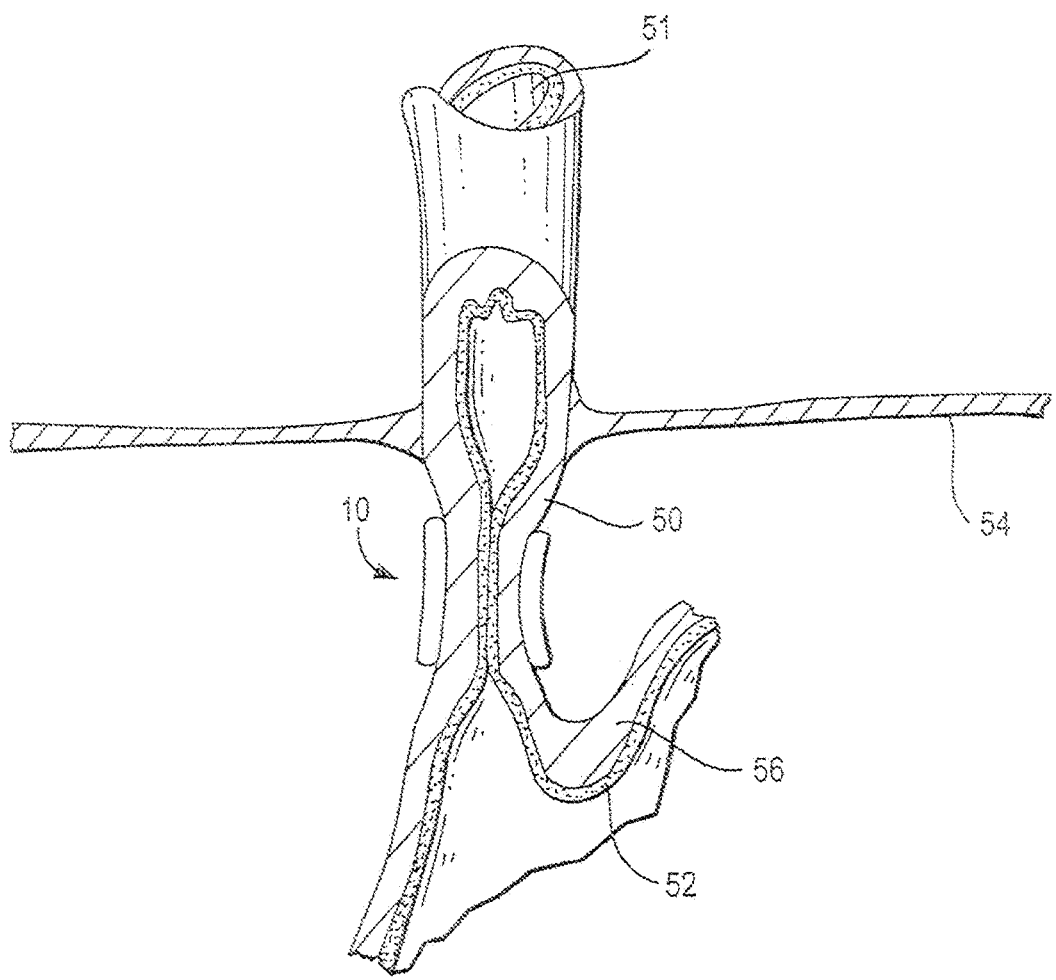
FIG. 10 is similar to a portion of FIG. 9 showing illustrative treatment of the patient's anatomy in accordance with the invention.

Turning now to more detail regarding how apparatus of the type shown and described above may be used as a medical implant in accordance with the invention, an illustrative use is as a treatment for gastro-esophageal reflux disorder or disease ("GERD"). In such a condition, the body structures that normally function to keep the lower part of the esophagus (near the stomach) closed, except when swallowing or when excessive pressure in the stomach needs to be relieved via the esophagus, is no longer functioning properly or adequately. This structure includes the lower esophageal sphincter ("LES"), possibly in cooperation with other tissue structures where the esophagus passes through the diaphragm (see FIG. 9, in which the reference numbers indicate the following: esophagus 50, lumen 51, mucosa 52, muscle wall 53, diaphragm 54, and stomach 55). FIG. 10 shows where the prosthesis 10 of this invention may be implanted in a patient to help restore normal functioning to the lower part of the esophagus. In the example shown in FIG. 10, apparatus 10 is disposed in a closed loop annularly around the outside of the esophagus between the diaphragm and the point where the esophagus enters the stomach. (Reference number 56 in FIG. 10 identifies additional muscle.)

Apparatus 10 can be implanted as shown, for example, in FIG. 10 in any of several ways. Typically, during the initial part of the implant procedure, apparatus 10 has not yet been made into a closed loop by connecting eyelet links 40. Instead, apparatus 10 is wrapped around the esophagus with eyelets 40 unconnected. When apparatus 10 is positioned as desired, eyelets 40 may be connected to one another (e.g., with a suture knot) to form the apparatus into a closed loop. If necessary or desirable to prevent excessive movement of apparatus 10 along the length of the esophagus, the apparatus may be secured (e.g., by one or more sutures, one or more clips, etc.) to the outside of the esophagus and/or to other adjacent tissue. This securement structure (e.g., sutures used for this purpose) may be dissolvable.

Any of several techniques can be used for introducing the implant 10 into the patient. For example, this may be done using open or relatively open surgery. As another example, the implant may be introduced into the patient using less invasive procedures such as laparoscopy and laparoscopic instruments. As still another example, the implant may be introduced trans-gastrically. In this technique the implant is introduced trans-orally into the esophagus, passed down the esophagus, and into the stomach. A dilator device is used to penetrate the wall of the stomach sufficient in size to allow the implant to be passed through this dilator into the space outside the stomach. The device, using instruments such as a stylet, can then be threaded around the lower esophagus. The implant can be connected into a closed loop with a suture, a clip, or stronger magnet beads located at each end. The implant may be modified to use an over-the-wire technique for this delivery method. In this case, a guide wire is placed around the distal esophagus and the implant is threaded over this wire once the wire is in position. The wire can then be removed.

It may be desirable to first measure or "size" the outer circumference of the esophagus where apparatus 10 is to be implanted. This may be done using one or more sizing instruments. When the desired implant size has been determined, an implant of that size may be implanted. Implants having different sizes may be provided by, for example, producing implants with different numbers of a given size bead 20, or by using beads 20 of different sizes to make implants of different sizes.

The implant may be medicated for any of several purposes. For example, such medication may include an antibiotic to combat infection, and/or the medication may include a steroid to promote appropriate healing.

Figure 6:
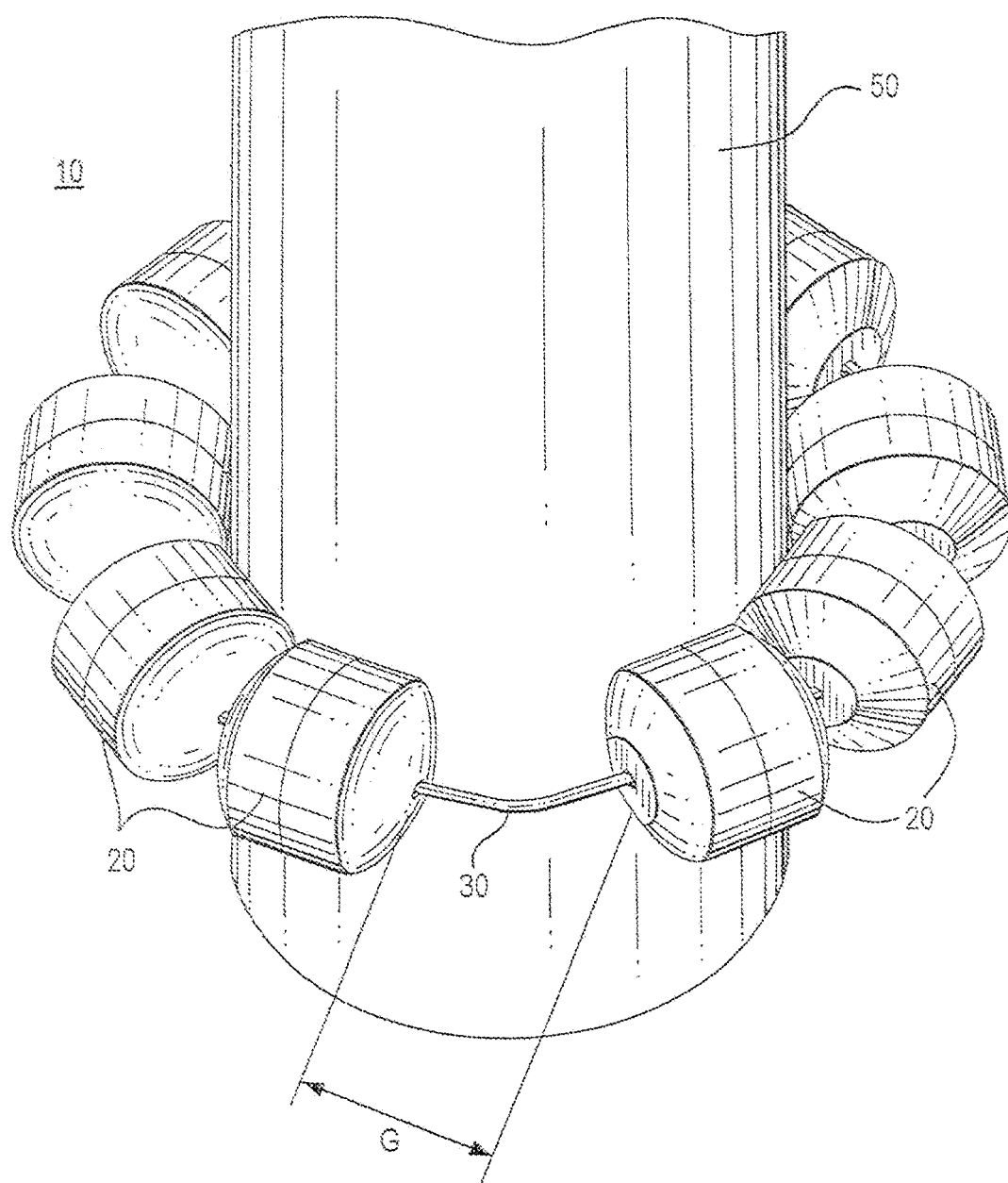
FIG. 6 is another view similar to FIG. 2, but shows another operating condition of the apparatus.

With regard to the annular size of the prosthesis, it is currently thought desirable in the treatment of GERD, for example, to slightly "under-size" apparatus 10 for the outside of the esophageal tissue structure to which the apparatus will be applied. This means selecting a size of prosthesis such that when the implant is in place in the patient, there is at least some space in the annular or circumferential direction between two (preferably only two) of beads 20. (See FIG. 6, which is intended to illustrate this condition of apparatus 10, implanted annularly around the outside of esophagus 50.) Indeed, it is thought especially preferable for the space (G in FIG. 6) between the two beads 20 mentioned in the preceding sentence to be relatively close to the maximum inter-bead spacing (i.e., the "link-length" in FIG. 8). This gives the implant an "at rest" force characteristic like that shown at or slightly to the left of point B in FIG. 8. In this way, the implant always applies some radial or annularly compressive force to the esophagus, but this force is relatively low. This force should be sufficient to significantly improve the "tone" and therefore the reflux-resisting closing of the esophagus. By thus slightly under-sizing the implant, it is thought that the "full-time" effectiveness of the implant in combating reflux is enhanced. However, this is only an optional aspect of the invention that others may prefer not to employ.

Continuing with the discussion of the example of applying apparatus 10 to a patient's esophagus, when the esophagus should be closed, the implant helps to keep it closed. However, when the patient swallows (e.g., a bolus of food), the implant annularly enlarges to the necessary extent to allow what has been swallowed down into the stomach. This may involve any number of beads 20 moving away from the adjacent bead(s). After any bolus has passed the plane of the implant, the implant resiliently returns to its initial, more annularly contracted condition. The same sequence of operations occur when excessive pressure in the stomach must be relieved through the esophagus. The implant annularly enlarges to vent the stomach, and then resiliently annularly contracts to return to its initial condition. The force exerted on the esophagus by the implant is preferably always large enough to help prevent reflux, but it is not so large as to impede swallowing or necessary venting of the stomach via the esophagus.

Over time, implanted apparatus 10 may become overgrown with tissue. However, this will not interfere with operation of the implant as described above. Tissue overgrowth as described in this paragraph may make it possible to form the links 30 of the prosthesis from an absorbable (e.g., suture) material such as polyglycolic acid and/or polylactic acid. In embodiments of this type the links would degrade and disappear over time. Once the implant is integrated to the external esophagus and a fibrous tissue cap has conformed to at least part of the beads, the function of the links between the beads may not be necessary.

Figure 11:
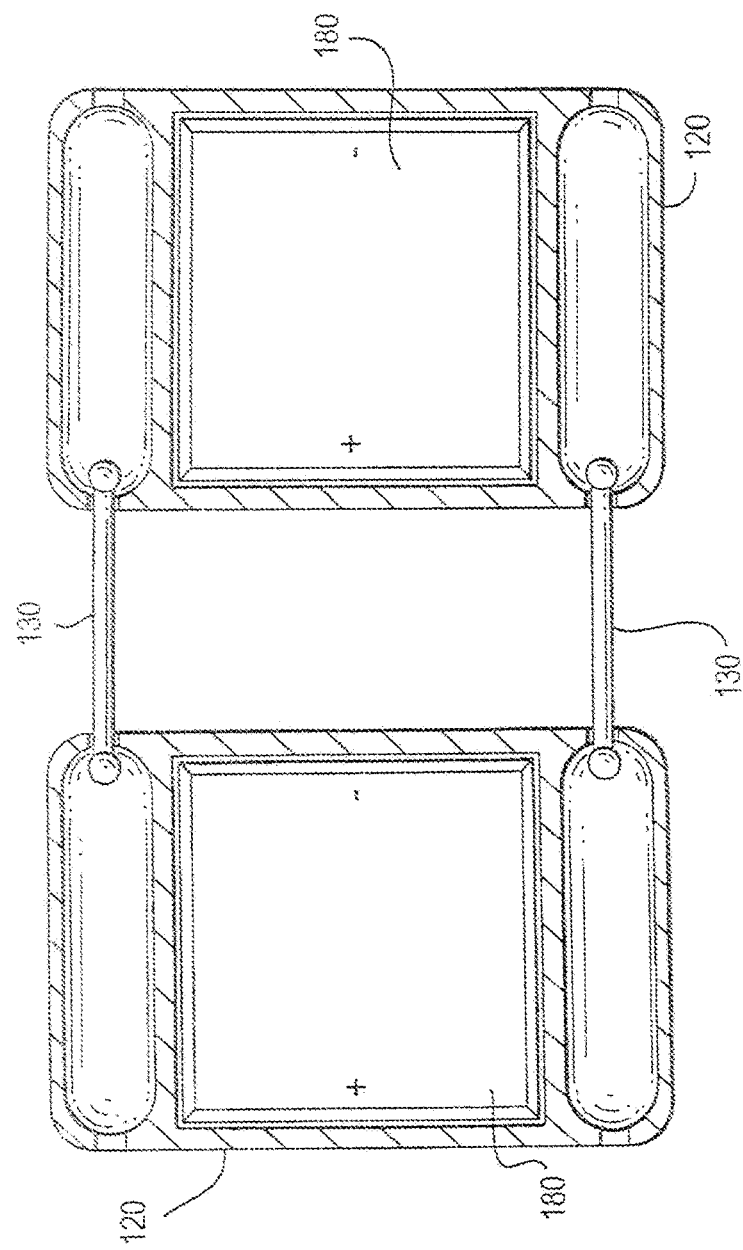
FIG. 11 is a simplified sectional view of a representative portion of another illustrative embodiment of prosthetic implant apparatus in accordance with the invention.
Figure 12:
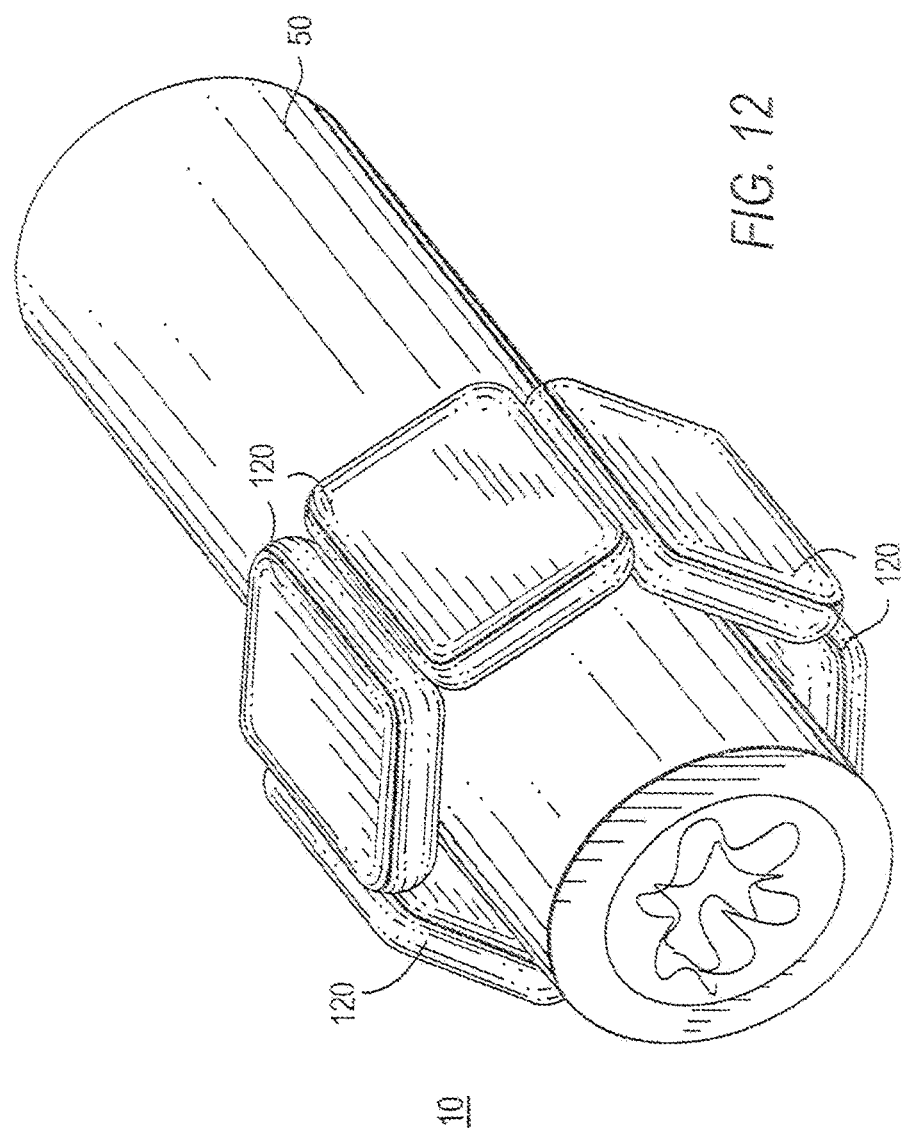
FIG. 12 is similar to FIG. 6 for an embodiment of the type shown in FIG. 11.

FIGS. 11 and 12 show an alternative embodiment in which beads 120 that can be flatter than beads 20 are used. Each of beads 120 includes a flat permanent magnet 180 and two parallel links 130 to each of the adjacent beads 120. Magnets 180 are polarized (+ and −) so that the magnets in adjacent beads magnetically attract one another. FIG. 12 shows an implant 10 that includes an annular array or closed loop of beads 120 disposed annularly and concentrically around the outside of esophagus 50. As compared to embodiments of the type illustrated by FIG. 1, for example, embodiments of the type illustrated by FIG. 12 may have the advantage of operating on tissue structure 50 along an axially longer portion of that structure.

Figure 13:
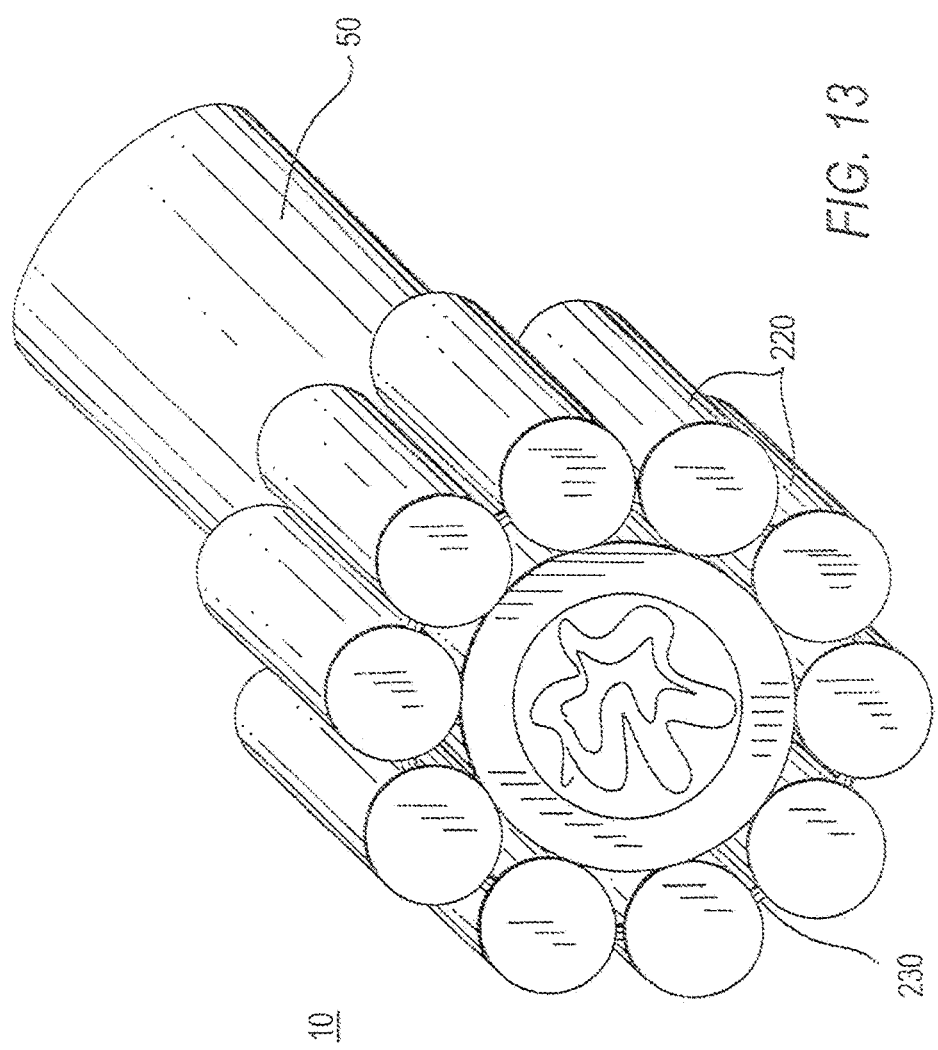
FIG. 13 is similar to FIG. 12, but shows yet another illustrative embodiment of prosthetic implant apparatus in accordance with the invention.
Figure 14:
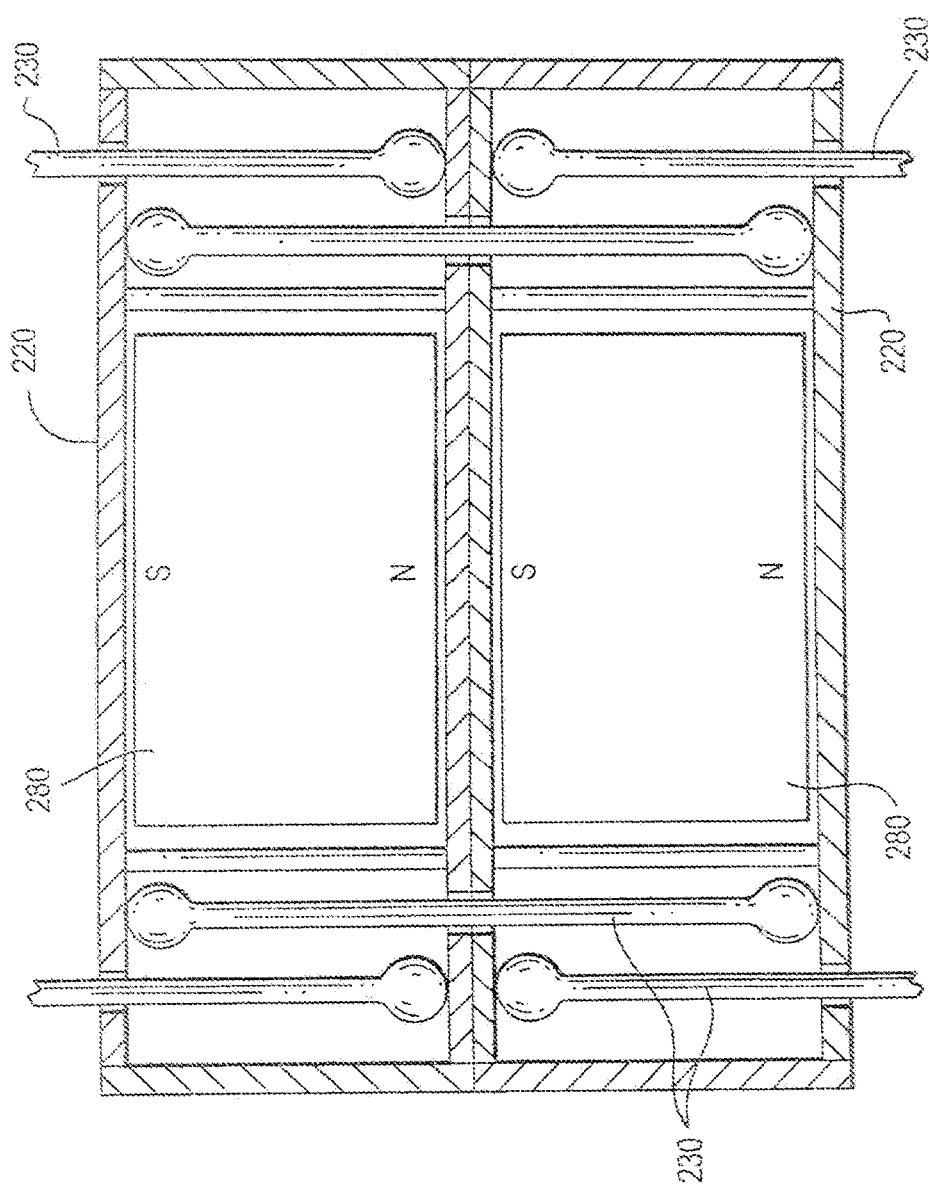
FIG. 14 is similar to FIG. 11 for an embodiment of the type shown in FIG. 13.

FIGS. 13 and 14 illustrate another embodiment that can be generally similar to the FIGS. 11 and 12 embodiment, except that in FIGS. 13 and 14 each bead 220 is a cylinder that is substantially parallel to the longitudinal axis of esophagus 50. As in FIGS. 11 and 12, in FIGS. 13 and 14 two parallel links 230 connect each bead 220 to each adjacent bead. Permanent magnets 280 in the beads are polarized to resiliently attract adjacent beads 220 toward one another. As compared to flat beads 120, cylindrical beads 220 may better conform to the annular outer surface of esophagus 50.

Figure 15:
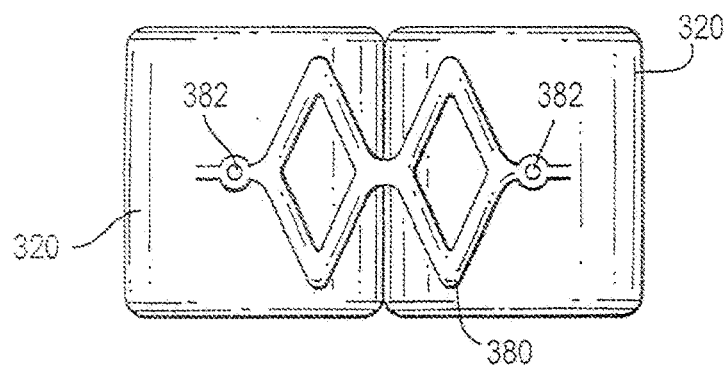
FIG. 15 is a simplified elevational view of a representative portion of still another illustrative embodiment of prosthetic implant apparatus in accordance with the invention.
Figure 16:
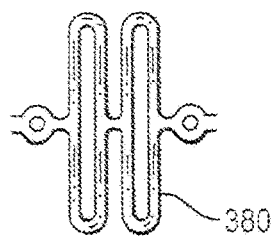
FIG. 16 is a simplified elevational view of one of the components shown in FIG. 15 in another condition of that component.

FIGS. 15-18 illustrate an alternative embodiment in which the attraction between adjacent beads 320 is provided by prestressed tension springs 380 between the beads. Springs 380 can be of an elastic material such as an elastic metal or an elastic polymer. Although FIGS. 15 and 17 only show two representative beads 320 and the representative spring 380 between those beads, it will be understood that more beads and springs are typically provided so that a closed loop of such beads (joined by such springs) can be formed, e.g., around the outside of a body tissue structure such as the esophagus. In the absence of beads 320, the relaxed state of a representative spring 380 is shown in FIG. 16. Thus spring 380 must be stretched (tensioned) somewhat to enable it to reach anchor points 382 on two adjacent and mutually contacting beads 320 as shown in FIG. 15. This means that spring 380 resiliently urges adjacent beads 320 toward one another even after those beads are in contact with one another.

Figure 17:
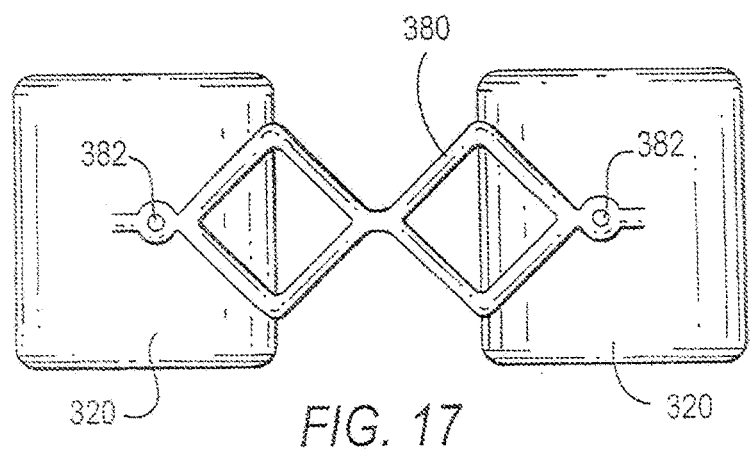
FIG. 17 is similar to FIG. 15, but shows another operating condition of the apparatus.
Figure 18:
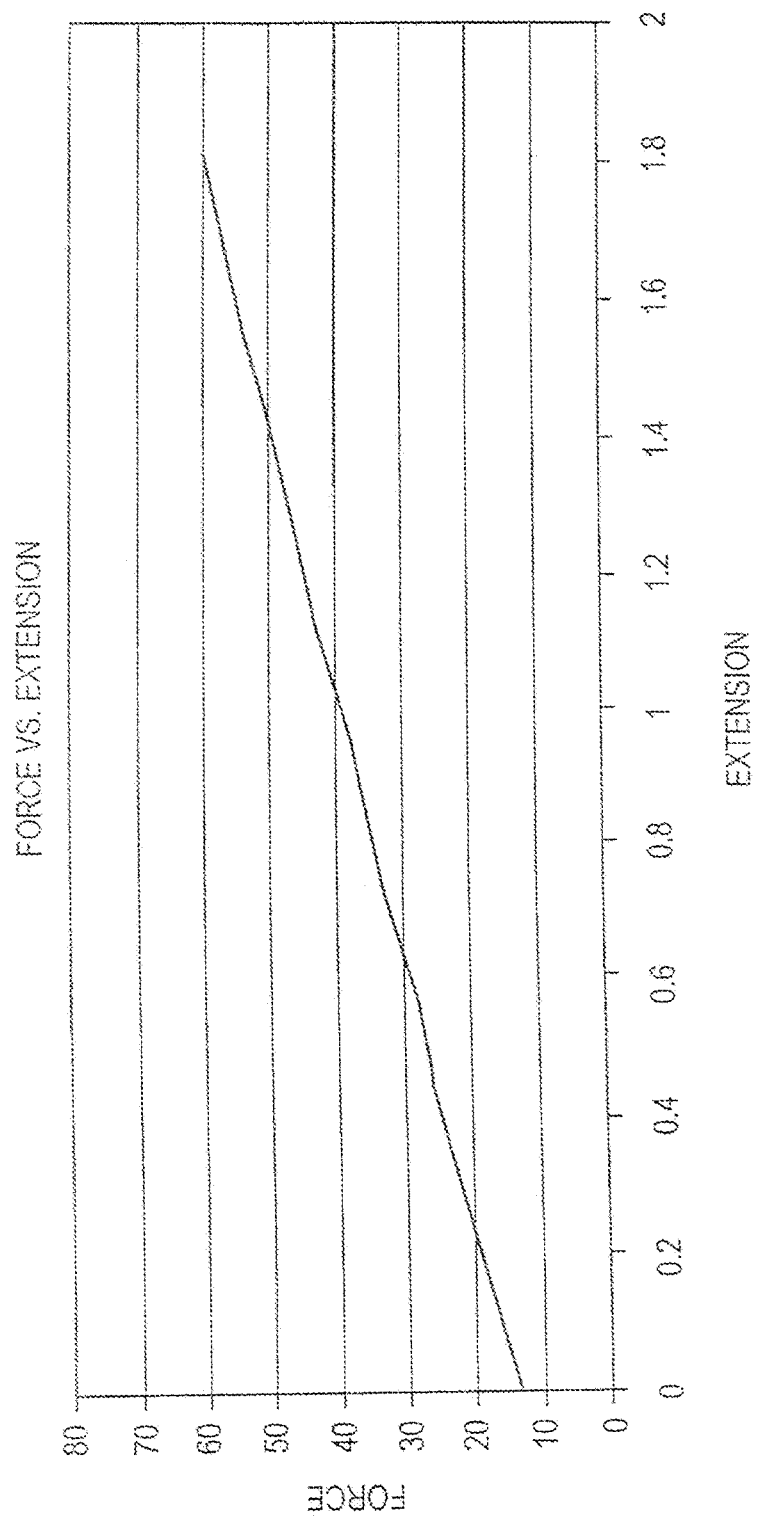
FIG. 18 is another graph that is useful in explaining certain aspects of the invention.

From the condition shown in FIG. 15, spring 380 allows adjacent beads 320 to move apart as shown, for example, in FIG. 17. Of course, as spring 380 stretches to thus allow beads 320 to move apart, the spring force urging beads 320 back toward one another increases in proportion to the spacing between the beads. This is illustrated by FIG. 18. As compared to the earlier-described magnetic embodiments, in which (at least theoretically) each inter-bead gap tends to open fully before another inter-bead gap begins to open, in spring embodiments as illustrated by FIGS. 15-17 all of the beads tend to move apart by similar amounts at the same time (assuming that all of the inter-bead springs 380 are of approximately the same strength). FIG. 18 is therefore indicative (depending on the horizontal and vertical scales employed) of both the force exerted as any one spring 380 is stretched or as the device as a whole is stretched (annularly enlarged).

Although FIGS. 15-17 show an illustrative spring embodiment in which springs are outside beads 320. It will be understood that springs for such an embodiment could instead be inside the beads. For example, prestressed compression coil springs inside the beads and around portions of the lengths of inter-bead links like 30, 130, or 230 in earlier FIGS. could be used to resiliently bias adjacent beads toward one another.

It will be noted that spring embodiments (e.g., as in FIGS. 15-17 or as otherwise described above) have the same advantage of self-limiting annular contraction as the earlier-described magnetic embodiments. Once all of the adjacent beads in a closed loop of spring-connected beads are in contact with one another, the loop cannot get any smaller and the interior of the structure inherently remains open (e.g., as in FIG. 1).

If desired, any of the above-described embodiments (including the magnetic embodiments) can be augmented to produce substantially equal spacing between adjacent beads at all times. FIGS. 19 and 20 illustrate an embodiment with such augmentation. In addition to whatever inter-bead attraction is employed, interconnected parallelogram linkages 490 are used between the beads 420 in this embodiment. Two crossing links 490 are pivotally connected to each bead at point 492. The ends of these links adjacent each next bead 320 are pivotally connected to the adjacent ends of the links 490 on that next bead at points 494. FIG. 19 shows the condition of the apparatus when adjacent beads 420 are close to or in contact with one another. FIG. 20 shows the condition of the apparatus when adjacent beads 420 are farther apart. Linkage 490/492/494 keeps the spacing between the adjacent beads substantially uniform, regardless of the amount of that spacing. Moreover, this result is achieved even for magnetic attraction between adjacent beads. This gives even a magnetic bead embodiment an overall force vs. displacement characteristic like that shown in FIG. 7, rather than like the characteristic shown in FIG. 8. (Of course, the horizontal scale in FIG. 7 will be different, depending on whether the FIG. depicts separation between two adjacent magnetically attracted beads or overall enlargement of a multibead magnetic prosthesis.)

Assuming that FIGS. 19 and 20 show an embodiment with magnetic beads 420, linkage 490/492/494 may take the place of other inter-bead links like 30/130/230 in earlier-depicted embodiments.

FIG. 29 shows an alternative embodiment in which the inter-bead links are provided by a continuous element 30 of elastic material. This element passes through each bead 20, and extends from bead to bead around the annular prosthesis 10. Element 30 may initially have two free ends (e.g., in the form of loops) that can be connected to one another to form an annular prosthesis. Beads 20 can move apart by stretching element 30. Element 30 resiliently urges beads 20 to move back into contact with one another. Element 30 is preferably somewhat prestressed even when all of beads 20 are in contact with one another. In the embodiment shown in FIG. 29, beads 20 are not at fixed locations along the length of element 30. In an alternative embodiment some or all of beads are secured to element 30 at predetermined locations along its length.

Another illustrative embodiment of the invention is shown in FIGS. 21-23. In this embodiment two magnetic structures 520 are attached, e.g., to the outside of esophagus 50, on respective opposite sides of the esophagus in a common plane that is substantially perpendicular to the longitudinal axis of the esophagus. For example, sutures 522 may be used to attach structures 520 to the esophagus. The implanted location of structures 520 may be as shown for apparatus 10 in FIG. 10. Each structure 520 is arched, with the concave side of the arch facing inwardly toward the adjacent outer surface of the esophagus. Structures 520 may be substantially rigid or somewhat flexible. However, if flexibility is employed, it is preferably not so great that structures 520 tend to completely lose their arched shape in use. In other words, if structures 520 are flexible, they are preferably resiliently biased to retain arched shapes like those shown in FIG. 22.

The arc length of each structure 520 is preferably sufficient that the ends of the one structure can contact the ends of the other structure beyond esophagus 50 (i.e., with no tissue of the esophagus between the contacting ends of the structures 520) as shown in FIG. 22. The size and amount of curvature of structures 520 is preferably sufficient to cause those structures to apply some closing pressure to esophagus 50 when the ends of the structures are in contact with one another as shown in FIG. 22. However, these parameters (especially the curvature) are also preferably sufficient to keep this FIG. 22 closing pressure on the esophagus from being too great, so as not to prevent opening of the esophagus for swallowing or normal stomach venting or to cause necrotic pressure on any tissue of the esophagus. As mentioned above, each of structures 520 is preferably rigid enough to hold at least a predetermined minimum arched shape.

Each of structures 520 includes one or more magnets 580 for magnetically attracting the other structure 520, e.g., across the esophagus. This magnetic attraction is strong enough to hold structures 520 together as shown in FIG. 22, except during swallowing or normal stomach venting. Accordingly, structures 520 are able to move apart as shown in FIG. 23 when the esophageal lumen needs to enlarge for swallowing or normal stomach venting.

Like the earlier-described embodiments, embodiments of the type shown in FIGS. 21-23 have the advantage of being self-limiting as they help esophagus 50 to close. Once the ends of structures 520 come into contact with one another as shown in FIG. 22, they apply no excessive additional pressure to the esophagus. A space always remains open between structures 520 for esophagus 50 to pass through, with no necrotic pressure being applied to any esophageal tissue between structures 520.

FIG. 24 is another view of certain components from the FIGS. 21-23 embodiment. FIG. 24 shows these components without any tissue being present, and also without magnets 580 in structures 520. FIG. 24 clearly shows how structures 520 cooperate to form a passageway therebetween and through which a tissue structure such as an esophagus can pass.

If desired, structures 520 like those shown in FIGS. 21-24 may be additionally or alternatively tethered to one another with thread, suture, or an elastic cord. The above-mentioned tethers may be absorbable.

FIGS. 25 and 26 show yet another illustrative embodiment of the invention. In this embodiment two pairs of magnets 680 are mounted side by side on the outer surface of a flexible "belt" 620 that is disposed annularly and concentrically around the outside of esophagus 50. FIG. 25 shows esophagus 50 open, and FIG. 26 shows the esophagus closed. Again, the apparatus of FIGS. 25 and 26 may be implanted as shown at 10 in FIG. 10. Sutures through belt 620 and into the esophagus may be used to hold the implanted apparatus in place.

When esophagus 50 opens as shown in FIG. 25 (e.g., for swallowing or excess stomach pressure venting), the enlarging esophagus stretches belt 620 so that the magnets 680 in one or both of the magnet pairs are pulled apart. FIG. 25 shows the magnets 680 in both pairs pulled apart, but if less opening of esophagus 50 is needed, only the magnets in one pair (i.e., the depicted upper pair or the depicted lower pair) may be pulled apart. When the esophagus can close again, the magnets 680 in the pairs go back together again as shown in FIG. 26.

The length of belt 620 between the closed magnet pairs (as in FIG. 26) is preferably selected so that the apparatus applies some additional closing pressure to esophagus 50, even when the esophagus is nominally closed. In this way the apparatus helps to prevent reflux from the stomach into the esophagus. On the other hand, no tissue is subjected to excessive, continuous pressure, such as could produce necrosis. For example, no tissue is trapped between the magnets 680 in either magnet pair, and the pressure on the esophagus from belt 620 is only sufficient to help keep the esophagus closed and is not dangerous to the tissue in any way. This pressure on the closed esophagus from belt 620 is also not so large as to interfere with swallowing or venting excessive pressure from the stomach. In other words, the apparatus readily changes from the FIG. 26 condition to the FIG. 25 condition during swallowing or during excessive stomach pressure venting.

Figure 27:
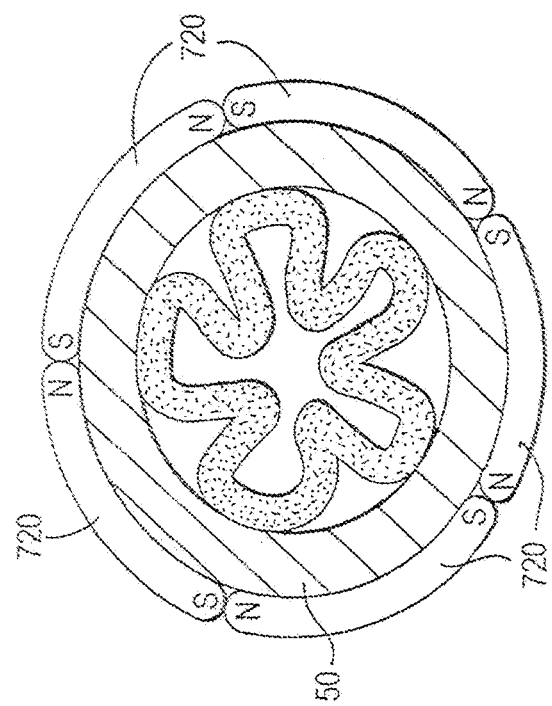
FIG. 27 is similar to FIG. 25 for still another illustrative embodiment of prosthetic implant apparatus in accordance with the invention.
Figure 28:
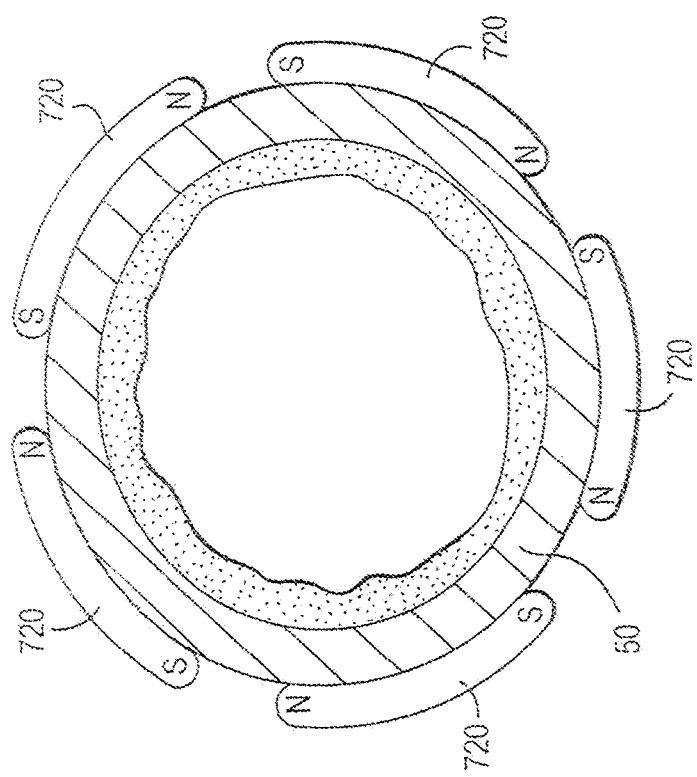
FIG. 28 is similar to FIG. 27, but shows another operating condition of the apparatus.

FIGS. 27 and 28 illustrate yet another embodiment. In this embodiment more than two arcuate magnetic beads 720 are individually secured to the outer surface of esophagus 50 in an annular array that is coaxial with the esophagus (e.g., at location 10 in FIG. 10). For example, sutures may be used to secure each bead 720 to the outer surface of the esophagus. The beads are magnetically polarized (N/S) so that each bead magnetically attracts its annularly adjacent neighbor beads.

When esophagus 50 is closed as shown in FIG. 28, annularly adjacent beads 720 contact one another and form a closed loop around the outside of the esophagus. This contact between the beads prevents any further annular contraction of the apparatus and thereby limits the amount of pressure the apparatus applies to esophagus 50. As in previously described embodiments, this most-closed condition of the apparatus preferably applies sufficient pressure to esophagus 50 to prevent reflux from the stomach into the esophagus. However, the attraction between annularly adjacent beads 720 in the most-closed (FIG. 28) condition of the apparatus is not so great as to prevent opening of the esophagus (e.g., as shown in FIG. 27) during swallowing or venting of excessive pressure from the stomach. When esophagus 50 opens for such purposes as swallowing or stomach venting, annularly adjacent beads 720 can separate from one another in the annular direction as shown in FIG. 27. When the esophagus again closes after the swallowing or stomach venting event, the magnetic attraction between annularly adjacent beads 720 helps that esophagus-closing proceed to a reflux-preventing conclusion as shown in FIG. 28 and as described above.

Such parameters as the number of beads 720, their shape (e.g., arched), etc., help ensure that when esophagus 50 is closed (FIG. 28), the interior of the loop of beads 720 remains open, with no strong tendency of the loop to collapse across the esophagus and apply excessive (e.g., necrotic) pressure to any esophageal tissue inside the loop of beads.

It will be understood that the foregoing is only illustrative of the principles of the invention, and that various modifications can be made by those skilled in the art without departing from the scope of the invention. For example, although application of the disclosed apparatus to a patient's esophagus in order to treat GERD has been given the most detailed attention herein, it will be understood that the invention has many other applications. For example, apparatus in accordance with the invention can be used around other body conduits, chambers, and/or sphincters in a patient's body. Just a few specific examples include use in treating urinary incontinence, anal incontinence, stomach size reduction, or as a completely artificial sphincter in the event that a natural sphincter has been removed or has wholly or largely ceased to function. Any of the structures shown and/or described herein as loops may be initially provided as open structures that are only formed into closed loops after placement around the target tissue structure. This principle is shown and described in detail in connection with embodiments like those illustrated by FIGS. 1-6, but it can be applied to any embodiment of the invention. Components that are described herein as magnets or permanent magnets do not all have to be actively magnetic. Some can be merely magnetizable (e.g., bodies of ferromagnetic material that are magnetically attracted to actual permanent magnets by becoming at least temporarily magnetized by the magnetic field from a nearby permanent magnet). Of course, there must always be at least one permanent magnet in any such system. Thus elements that are referred to herein as magnets or magnetic may be either actively magnetic or passively magnetic (i.e., temporarily magnetizable by a magnetic field from another source).

The invention claimed is:

1. A medical implant, the medical implant comprising:
   (a) a plurality of beads, wherein each bead comprises:
      (i) a housing assembly defining a first hollow interior and a second hollow interior positioned concentrically around the first hollow interior, wherein the first hollow interior extends from a first aperture to a second aperture, and
      (ii) at least one magnet disposed within the second hollow interior; and
   (b) a plurality of links joining the beads together, wherein portions of the links are slidably disposed in corresponding first hollow interiors of the beads such that the plurality of beads are operable to transition between a constricted configuration and an expanded configuration, wherein the housing assemblies of adjacent beads in the plurality of beads are configured to abut against each other in the constricted configuration.

2. The medical implant of claim 1, wherein the first hollow interior is isolated from the second hollow interior.

3. The medical implant of claim 1, wherein the housing assembly of each bead comprises a first housing component and a second housing component, wherein the first housing component and the second housing component are configured to mate together to define the first hollow interior and the second hollow interior.

4. The medical implant of claim 3, wherein the first housing component defines the first aperture, wherein the second housing component defines the second aperture.

5. The medical implant of claim 4, wherein the first housing component further comprises a post, wherein the post defines the first hollow interior.

6. The medical implant of claim 4, wherein the housing assembly further comprises a washer-like cap associated with the second aperture.

7. The medical implant of claim 3, wherein the first housing component comprises a cup shape.

8. The medical implant of claim 1, wherein the at least one magnet comprises a toroidal shape.

9. The medical implant of claim 1, wherein the first aperture is located at a first end of the housing assembly, wherein the second aperture is located at a second end of the housing assembly, wherein the first end comprises a convex profile, wherein the second end comprises a substantially flat profile.

10. The medical implant of claim 9, wherein the at least one magnet of each bead in the plurality of beads biases the plurality of beads toward the constricted configuration, wherein the medical implant is sized to bear radially inwardly against an esophagus in the constricted configuration.

11. The medical implant of claim 1, wherein at least one link in the plurality of links defines a lateral bend.

12. The medical implant of claim 1, wherein at least one link in the plurality of links terminate in a first stop and a second stop on opposite ends.

13. The medical implant of claim 12, wherein the first stop of the at least one link is contained within the first hollow interior of a first bead, wherein the second stop of the at least one link is contained within the first hollow interior of an adjacent bead.

14. A medical implant, the medical implant comprising:
   (a) a plurality of beads, wherein each bead comprises:
      (i) a housing assembly defining a first hollow interior and a second hollow interior positioned concentrically around the first hollow interior, wherein the first hollow interior extends from a first aperture to a second aperture, and
      (ii) at least one magnet disposed within the second hollow interior, wherein adjacent beads in the plurality of beads are magnetically attracted to each other; and
   (b) a plurality of links joining the beads together, wherein the plurality of links each terminate into a stop housed within the first hollow interior, wherein portions of the links are slidably disposed in corresponding first hollow interiors of the beads such that the plurality of beads are operable to transition between a constricted configuration and an expanded configuration, wherein the stop of each link in the plurality of links is configured to abut against either the first aperture or the second aperture in the expanded configuration.

15. The medical implant of claim 14, wherein the housing assembly further comprises a post defining the first hollow interior.

16. The medical implant of claim 14, wherein at least one link in the plurality of links comprise an elongated lateral bend.

17. The medical implant of claim 14, wherein the plurality of beads are configured to radially expand and contract between the constricted configuration and the expanded configuration.

18. The medical implant of claim 14, wherein the housing assemblies of adjacent beads are configured to abut against each other in the constricted configuration.

19. The medical implant of claim 14, wherein the housing assembly comprises a first cup shaped housing component and a second cup shaped housing component configured to mate together.

20. A medical implant, the medical implant comprising:
   (a) a plurality of beads, wherein each bead comprises:
      (i) a housing assembly defining a first hollow interior and a second hollow interior positioned concentrically around the first hollow interior, wherein the first hollow interior extends from a first aperture to a second aperture, and (ii) at least one magnet disposed within the second hollow interior, wherein adjacent beads in the plurality of beads are magnetically attracted to each other; and (b) a plurality of links joining the beads together, wherein the plurality of links each terminated into a stop housed within the first hollow interior, wherein portions of the links are slidably disposed in corresponding first hollow interiors of the beads such that the plurality of beads are operable to transition between a constricted configuration and an expanded configuration, wherein the housing assemblies of adjacent beads in the plurality of beads are configured to abut against each other in the constricted configuration, wherein the stop of each link in the plurality of links is configured to abut against either the first aperture or the second aperture in the expanded configuration.

* * * * *